US012144899B2

(12) United States Patent
Borsadia et al.

(10) Patent No.: US 12,144,899 B2
(45) Date of Patent: Nov. 19, 2024

(54) TETRABENAZINE TRANSDERMAL DELIVERY DEVICE

(71) Applicant: SHINKEI THERAPEUTICS LLC, Princeton, NJ (US)

(72) Inventors: Suresh Borsadia, Plainsboro, NJ (US); Kalpana Patel, West Windsor, NJ (US); Hock S. Tan, East Brunswick, NJ (US)

(73) Assignee: SHINKEI THERAPEUTICS, INC., Princeton, NJ (US)

( * ) Notice: Subject to any disclaimer, the term of this patent is extended or adjusted under 35 U.S.C. 154(b) by 1042 days.

(21) Appl. No.: 17/050,230

(22) PCT Filed: Apr. 24, 2019

(86) PCT No.: PCT/US2019/028900
§ 371 (c)(1),
(2) Date: Oct. 23, 2020

(87) PCT Pub. No.: WO2019/209940
PCT Pub. Date: Oct. 31, 2019

(65) Prior Publication Data
US 2021/0128490 A1 May 6, 2021

Related U.S. Application Data

(60) Provisional application No. 62/662,456, filed on Apr. 25, 2018.

(51) Int. Cl.
| | |
|---|---|
| *A61K 9/70* | (2006.01) |
| *A61K 31/4745* | (2006.01) |
| *A61K 47/14* | (2017.01) |
| *A61K 47/32* | (2006.01) |
| *A61K 47/34* | (2017.01) |
| *A61K 47/38* | (2006.01) |

(52) U.S. Cl.
CPC ........ *A61K 9/7061* (2013.01); *A61K 31/4745* (2013.01); *A61K 47/14* (2013.01); *A61K 47/32* (2013.01); *A61K 47/34* (2013.01); *A61K 47/38* (2013.01)

(58) Field of Classification Search
None
See application file for complete search history.

(56) References Cited

U.S. PATENT DOCUMENTS

| | | |
|---|---|---|
| 6,221,383 B1 | 4/2001 | Miranda et al. |
| 6,562,363 B1 | 5/2003 | Mantelle et al. |
| 8,524,733 B2 | 9/2013 | Gant et al. |
| 9,682,068 B2 | 6/2017 | Deshmukh et al. |
| 9,782,398 B2 | 10/2017 | Hoare |
| 10,363,228 B2 | 7/2019 | Eifler et al. |
| 10,857,148 B2 | 12/2020 | O'Brien et al. |
| 10,874,648 B2 | 12/2020 | O'Brien et al. |
| 10,898,449 B2 | 1/2021 | Mohr et al. |
| 10,959,996 B2 | 3/2021 | Stamler et al. |
| 2002/0077437 A1* | 6/2002 | Silverberg ........... C09J 133/062 548/554 |
| 2006/0078604 A1* | 4/2006 | Kanios .................. A61K 47/34 424/449 |
| 2008/0108645 A1 | 5/2008 | Tridgett et al. |
| 2008/0319000 A1 | 12/2008 | Tridgett et al. |
| 2012/0208773 A1 | 8/2012 | Duffield et al. |
| 2014/0242063 A1 | 8/2014 | Duffield et al. |
| 2015/0148759 A1* | 5/2015 | Friedrich ............. A61K 31/137 604/307 |
| 2016/0008294 A1 | 1/2016 | Hille et al. |
| 2016/0113908 A1 | 4/2016 | Deshmukh et al. |
| 2016/0128949 A1 | 5/2016 | Kanios et al. |
| 2016/0346270 A1 | 12/2016 | Stamler |
| 2017/0071932 A1 | 3/2017 | O'Brien |
| 2017/0239357 A1* | 8/2017 | Ronchi ................ A61K 8/0233 |
| 2017/0340578 A1* | 11/2017 | Scasso ................ A61K 31/381 |
| 2018/0064701 A1 | 3/2018 | Stamler et al. |
| 2018/0280359 A1 | 10/2018 | Duffield et al. |
| 2018/0280374 A1 | 10/2018 | Duffield et al. |
| 2018/0311362 A1* | 11/2018 | Takita ................. A61K 9/7053 |
| 2018/0318281 A1 | 11/2018 | Stamler et al. |

(Continued)

FOREIGN PATENT DOCUMENTS

| | | |
|---|---|---|
| CN | 104470585 A | 3/2015 |
| CN | 106456629 | 2/2017 |

(Continued)

OTHER PUBLICATIONS

Yao et al. European Journal of Medicinal Chemistry 2011 46:1841-1848 (Year: 2011).*
"DURO-TAK and GELVA Transdermal Pressure Sensitive Adhesives", Henkel Corporation, Sep. 3, 2013, 2 pages.
C. Kenney, et al., "Tetrabenazine in the treatment of hyperkinetic movement disorders.", Expert Review of Neurotherapeutics, vol. 6, No. 1, Jan. 2006, 1 page (Abstract).
International Search Report for PCT/US2019/028900 dated Aug. 7, 2019, 3 pages.

(Continued)

*Primary Examiner* — Melissa S Mercier
*Assistant Examiner* — Caralynne E Helm
(74) *Attorney, Agent, or Firm* — NIXON & VANDERHYE, PC

(57) ABSTRACT

Provided herein are transdermal delivery devices comprising tetrabenazine, a deuterated tetrabenazine, or a combination thereof. Also provided herein are pharmaceutical compositions, such as adhesive compositions, comprising tetrabenazine, a deuterated tetrabenazine, or a combination thereof, for example, homogenously dispersed in an adhesive, such as a pressure sensitive adhesive. Further provided herein are methods of using the transdermal delivery devices or pharmaceutical compositions, for example, for treating a hyperkinetic movement disorder.

27 Claims, 3 Drawing Sheets

(56) References Cited

U.S. PATENT DOCUMENTS

Figure 1:
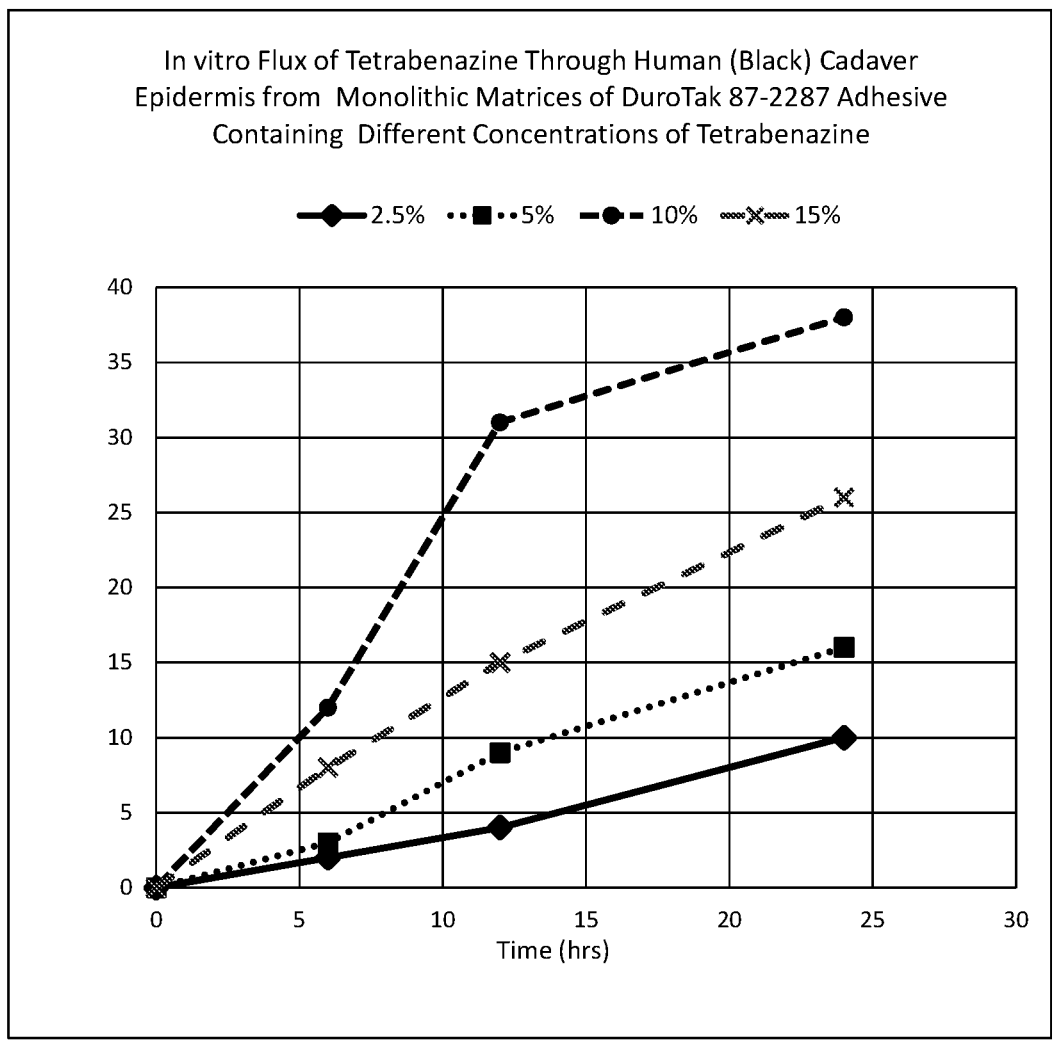

| | | |
|---|---|---|
| 2019/0015396 A1 | 1/2019 | O'Brien |
| 2019/0111035 A1 | 4/2019 | Duffield et al. |
| 2019/0374521 A1 | 12/2019 | Tabuteau |
| 2019/0381016 A1 | 12/2019 | O'Brien et al. |
| 2020/0000785 A1 | 1/2020 | Waters et al. |
| 2020/0093808 A1 | 3/2020 | O'Brien et al. |
| 2020/0155535 A1 | 5/2020 | Wesolowska et al. |
| 2020/0179352 A1 | 6/2020 | O'Brien |
| 2020/0206215 A1 | 7/2020 | Hoare et al. |

FOREIGN PATENT DOCUMENTS

| | | | |
|---|---|---|---|
| CN | 107624067 | | 1/2018 |
| CN | 110087640 | | 8/2019 |
| CN | 112165942 | | 1/2021 |
| JP | S63313723 | A | 12/1988 |
| JP | H09511987 | A | 12/1997 |
| JP | H1179980 | A  * | 3/1999 |
| JP | 2001517493 | A | 10/2001 |
| JP | 2012503010 | A | 2/2012 |
| JP | 2013501810 | A | 1/2013 |
| JP | 2013528631 | A | 7/2013 |
| JP | 2015515475 | A | 5/2015 |
| JP | 2016520638 | A | 7/2016 |
| JP | 2017514850 | | 6/2017 |
| WO | 2006053067 | A2 | 5/2006 |
| WO | 2011019956 | | 2/2011 |
| WO | 2013/152105 | | 10/2013 |
| WO | 2015171802 | A1 | 11/2015 |
| WO | 2017003935 | A1 | 1/2017 |
| WO | 2019020994 | A1 | 10/2019 |
| WO | 2019209940 | | 10/2019 |
| WO | 2019241555 | A1 | 12/2019 |

OTHER PUBLICATIONS

Written Opinion of the ISA for PCT/US2019/028900 dated Aug. 7, 2019, 5 pages.

David P. Kanios: "Technology Advancements in Passive Transdermal Drug Delivery Systems Utilizing Pressure Sensitive Adhesives and Polymeric Components", Aug. 3, 2009, XP055087317, Retrieved from the Internet: URL : http://www.pstc.org/files/public/Kanios09.pdf.

David P. Kanios: "Effect of Non-Functional / Non-Reactive Pressure Sensitive Adhesives in Transdermal Drug Delivery Systems", Nov. 2, 2005, XP055087316, Retrieved from the Internet: URL:http://www.pstc.org/files/public/Kanios.pdf.

Auchter G et al: "Acrylic adhesives", Jan. 1, 1999, Handbook of Pressure Sensitive Adhesive Technology, Warwick, RI : SATAS & ASSOCIATES, 1999, US, pp. 444-449, XP009166896, ISBN: 978-0-9637993-3-3.

U.S. Appl. No. 17/770,857, filed Apr. 21, 2022, Raval et al., related application.

* cited by examiner

TETRABENAZINE TRANSDERMAL DELIVERY DEVICE

CROSS REFERENCE TO RELATED APPLICATIONS

This application is the U.S. national phase of International Application No. PCT/US2019/028900 filed Apr. 24, 2019 which designated the U.S. and claims priority to U.S. Provisional Patent Application No. 62/662,456 filed Apr. 25, 2018, the entire contents of each of which are hereby incorporated by reference.

BACKGROUND OF THE INVENTION

Field of the Invention

In various embodiments, the present invention generally relates to transdermal delivery devices comprising tetrabenazine and/or a deuterated tetrabenazine, pharmaceutical compositions comprising tetrabenazine and/or a deuterated tetrabenazine, methods of preparing the same, and methods of using the same.

Background Art

Tetrabenazine is a vesicular monoamine transporter 2 (VMAT2) inhibitor. Tetrabenazine was approved by the U.S. Food and Drug Administration (FDA) as Xenazine® tablet for oral use, indicated for the treatment of chorea associated with Huntington's disease. The active ingredient in Xenazine® tablet is a racemic mixture of (3R,11bR)-1,3,4,6,7,11b-Hexahydro-9,10-dimethoxy-3-(2-methylpropyl)-2H-benzo[a]quinolizin-2-one (hereinafter "R,R-tetrabenazine") and (3S,11bS)-1,3,4,6,7,11b-hexahydro-9,10-dimethoxy-3-(2-methylpropyl)-2H-benzo[a]quinolizin-2-one (hereinafter "S,S-tetrabenazine").

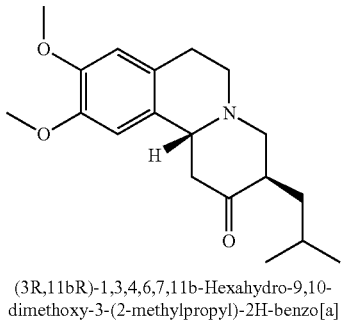

(3R,11bR)-1,3,4,6,7,11b-Hexahydro-9,10-dimethoxy-3-(2-methylpropyl)-2H-benzo[a]quinolizin-2-one

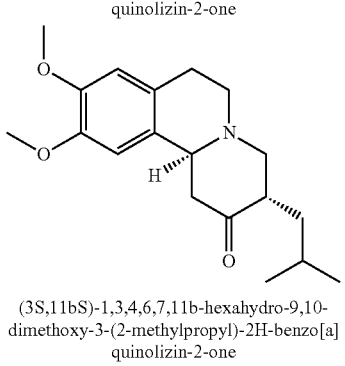

(3S,11bS)-1,3,4,6,7,11b-hexahydro-9,10-dimethoxy-3-(2-methylpropyl)-2H-benzo[a]quinolizin-2-one In 2017, the FDA approved a deuterated tetrabenazine, deutetrabenazine, as Austedo™ tablets for oral use, which is also indicated for the treatment of chorea associated with Huntington's disease. The active ingredient in Austedo™ tablet is a selectively deuterium-substituted, stable, non-radioactive isotopic form of tetrabenazine in which the six hydrogen atoms on the two O-linked methyl groups have been replaced with deuterium atoms (i.e. $-OCD_3$ rather than $-OCH_3$ moieties). The active ingredient in Austedo™ tablet is also a racemic mixture.

BRIEF SUMMARY OF THE INVENTION

The FDA approved labels for Xenazine® and Austedo™ each contains a blackbox warning against potential risks of depression and suicidality. For both products, the actual dosing needs to be monitored and titrated. For example, the Xenazine® label indicates that for patients requiring doses above 50 mg per day, the patients should be genotyped the drug metabolizing enzyme CYP2D6 to determine if the patient is a poor metabolizer (PM) or an extensive metabolizer (EM). For poor metabolizers, the maximum daily dose can only be 50 mg, with the maximum single dose of 25 mg. Whereas for extensive metabolizers or intermediate metabolizers, the maximum daily dose is 100 mg, with the maximum single dose of 37.5 mg. Similarly, the Austedo™ label also states that for poor metabolizers, the maximum daily dose can only be 36 mg, with two single doses of 18 mg.

Despite recent advances, tetrabenazine/deutetrabenazine medication remains complicated, which involves dose titration to reduce potential dose-related side effects. Thus, novel tetrabenazine formulations and dosing options are needed.

In various embodiments, the present invention provides a transdermal delivery device comprising tetrabenazine and/or a deuterated tetrabenazine (e.g., deutetrabenazine). In various embodiments, the present invention also provides a pharmaceutical composition (e.g., an adhesive composition) comprising tetrabenazine and/or a deuterated tetrabenazine (e.g., deutetrabenazine). In various embodiments, the present invention further provides a method of preparing or using a transdermal delivery device or a pharmaceutical composition comprising tetrabenazine and/or a deuterated tetrabenazine (e.g., deutetrabenazine).

Certain embodiments of the present invention are directed to transdermal delivery devices. Typically, the transdermal delivery device comprises a backing layer, a drug layer comprising a drug chosen from tetrabenazine, a deuterated tetrabenazine, or a combination thereof, for example, in an amount of about 2% to about 30% by weight of the drug layer, and an adhesive layer, which defines an active surface area. The transdermal delivery device is generally designed to have certain flux characteristics, for example, any of those defined herein. The active surface area can determine the amount of drug administered/delivered. Typically, the active surface area can range from about 5 cm² to about 300 cm², for example, about 10 cm² to about 100 cm².

The transdermal delivery device herein is not limited to any specific patch designs. For example, the transdermal delivery device herein can be a drug-in-adhesive patch, drug-in-reservoir patch, or another patch design. In some embodiments, the transdermal delivery device can be a drug-in-adhesive patch, for example, a single layer DIA patch. In some embodiments, the transdermal delivery device can comprise more than one drug layer, for example, two or more drug-in-adhesive layer. In some embodiments, the transdermal delivery device can be a drug-in-reservoir patch, for example, the drug layer is a reservoir comprising tetrabenazine and/or a deuterated tetrabenazine.

The drug layer can comprise tetrabenazine, deuterated tetrabenazine, or a combination thereof. In any of the embodiments described herein, the drug layer can comprise tetrabenazine, for example, a substantially pure R,R-tetrabenazine. In some embodiments, tetrabenazine (e.g., a substantially pure R,R-tetrabenazine) is the only active ingredient in the drug layer. In any of the embodiments described herein, the drug layer can comprise deutetrabenazine, for example, a substantially pure R,R-deutetrabenazine. In some embodiments, deutetrabenazine (e.g., a substantially pure R,R-deutetrabenazine) is the only active ingredient in the drug layer. In some embodiments, the drug layer comprises tetrabenazine, deuterated tetrabenazine, or a combination thereof, in an amount of about 2% to about 30% (e.g., about 2%, about 2.5%, about 5%, about 8%, about 10%, about 15%, about 18%, about 20%, about 25%, about 30%, or any ranges in between the recited values) by weight of the drug layer. In some specific embodiments, the drug layer comprises tetrabenazine, deuterated tetrabenazine, or a combination thereof, in the amount of about 2%, about 2.5%, about 5%, about 8%, about 10%, about 15%, or about 20% by weight of the drug layer. In some embodiments, the drug layer can optionally include one or more other ingredients, for example, selected from skin permeation enhancers, humectants, plasticizers, antioxidants, anti-irritants, gel-forming agents, drug release modifiers, solvents, crystallization inhibitors, and additional active ingredients. In some embodiments, the drug layer can have a coat weight of about 0.1 g/cm$^2$ to about 0.90 g/cm$^2$ (e.g., about 0.1 g/cm$^2$ to about 0.5 g/cm$^2$) active surface area.

In some embodiments, the drug layer comprises tetrabenazine, deuterated tetrabenazine, or a combination thereof dispersed (e.g., homogenously dispersed) in an adhesive (e.g., a pressure sensitive adhesive). Suitable pressure sensitive adhesives are described herein. In some embodiments, the pressure sensitive adhesive can include a polyisobutylene (PIB) adhesive, a silicone polymer adhesive (e.g., Bio-7-4202), an acrylate copolymer adhesive (e.g., DuroTak 87-2287), or a combination thereof. In some embodiments, the pressure sensitive adhesive can be a non-reactive acrylate adhesive, for example, an acrylate adhesive that has no functional groups containing reactive hydrogen moieties, or an acrylate adhesive that has no functional groups selected from epoxy, —OH, —COOH, and combinations thereof.

The adhesive layer is typically formulated such that the transdermal delivery device can adhere to the skin of a user for a desired period of time. For example, in some embodiments, the transdermal delivery device is capable of adhering continuously to the skin of a user for about 8 hours, about 12 hours, about 18 hours, about 24 hours, about 2 days, about 3 days, about 4 days, about 5 days, about 6 days, or about 7 days or more.

Certain embodiments of the present invention are also directed to an adhesive composition. In some embodiments, the adhesive composition comprises a drug chosen from tetrabenazine, deuterated tetrabenazine (e.g., deutetrabenazine), and combinations thereof in an adhesive. In some embodiments, the drug is homogenously dispersed in the adhesive (e.g., a pressure sensitive adhesive). In some embodiments, the pressure sensitive adhesive can be a non-reactive acrylate adhesive, for example, an acrylate adhesive that has no functional groups containing reactive hydrogen moieties, or an acrylate adhesive that has no functional groups selected from epoxy, —OH, —COOH, and combinations thereof. In some embodiments, the pressure sensitive adhesive comprises a polyisobutylene (PIB) adhesive, a silicone polymer adhesive, an acrylate copolymer adhesive, or a combination thereof. In some embodiments, the adhesive composition comprises tetrabenazine (e.g., a substantially pure R,R-tetrabenazine) in an amount of about 2% to about 30% by weight of the adhesive composition. In some embodiments, the adhesive composition comprises deutetrabenazine (e.g., a substantially pure R,R-deutetrabenazine) in an amount of about 2% to about 30% by weight of the adhesive composition. In some embodiments, the active ingredient is present in an amount of about 2% to about 7% by weight. In some embodiments, the adhesive composition is free of a permeation enhancer, for example, free of isopropyl myristate. However, in some embodiments, the adhesive composition further comprises a permeation enhancer. In some embodiments, the adhesive composition can comprise an antioxidant, e.g., a gallate antioxidant, such as propyl gallate. In some embodiments, the adhesive composition can comprise a crystallization inhibitor, such as a polyvinylpyrrolidone polymer, a cross-linked polyvinylpyrrolidone polymer, a polyvinylpyrrolidone copolymer, a cellulose based polymer, a polycarboxylic acid polymer, a polymethacrylate, a polyethylene glycol, polyvinyl acetate and polyvinylcaprolactame-based graft copolymer (PVAc-PVCap-PEG), or a combination thereof. In some preferred embodiments, the adhesive composition comprises a crystallization inhibitor which is a copolymer of butyl methacrylate and methyl methacrylate. In some embodiments, the adhesive composition comprises a crystallization inhibitor which is a polyethylene glycol, polyvinyl acetate and polyvinylcaprolactame-based graft copolymer. In some embodiments, the adhesive composition is capable of adhering continuously to the skin of a user for an extended period of time selected from about 8 hours, about 12 hours, about 18 hours, about 24 hours, about 2 days, about 3 days, about 4 days, about 5 days, about 6 days, or about 7 days or more. The adhesive composition described herein can be used for a transdermal delivery device. For example, in some embodiments, the transdermal delivery device can include any of the adhesive compositions described herein, a backing layer, and a release liner.

In some embodiments, the present invention provides a method of transdermally administering tetrabenazine, deuterated tetrabenazine, or a combination thereof to a subject (e.g., human subject) in need thereof. In some embodiments, the method comprises applying any of the transdermal delivery devices or pharmaceutical compositions (e.g., adhesive compositions) to the subject, for example, to the skin of the subject.

In some embodiments, the present invention also provides a method of inhibiting VMAT-2 in a subject in need thereof. In some embodiments, the method comprises applying any of the transdermal delivery devices or pharmaceutical compositions (e.g., adhesive compositions) to the subject, for example, to the skin of the subject.

In some embodiments, the present invention also provides a method of treating a vesicular monoamine transporter isoform 2 (VMAT2) mediated disease or disorder in a subject (e.g., a human subject) in need thereof. In some embodiments, the method comprises applying any of the transdermal delivery devices or pharmaceutical compositions (e.g., adhesive compositions) to the subject, for example, to the skin of the subject.

In some specific embodiments, the present invention provides a method of treating a hyperkinetic movement disorder in a subject (e.g., human subject) in need thereof. In some embodiments, the method comprises transdermally administering a therapeutically effective amount of tetrabenazine and/or deuterated tetrabenazine to the subject. In some embodiments, the method comprises applying any of the transdermal delivery devices or pharmaceutical compositions (e.g., adhesive compositions) to the subject, for example, to the skin of the subject. In some embodiments, the hyperkinetic movement disorder is a chronic hyperkinetic movement disorder. In some embodiments, the hyperkinetic movement disorder is chorea associated with Huntington's disease, Wilson's disease, Tourette syndrome, restless leg syndrome, tardive dyskinesia, and/or a tic. In some embodiments, the hyperkinetic movement disorder is chorea associated with Huntington's disease.

BRIEF DESCRIPTION OF THE DRAWINGS/FIGURES

FIG. 1 presents graphs showing the in vitro flux of tetrabenazine through human (Black) cadaver epidermis from monolithic matrices of Duro-Tak 87-2287 adhesive containing tetrabenazine at different concentrations (10%, 15%, 5%, and 2.5%).

Figure 2:
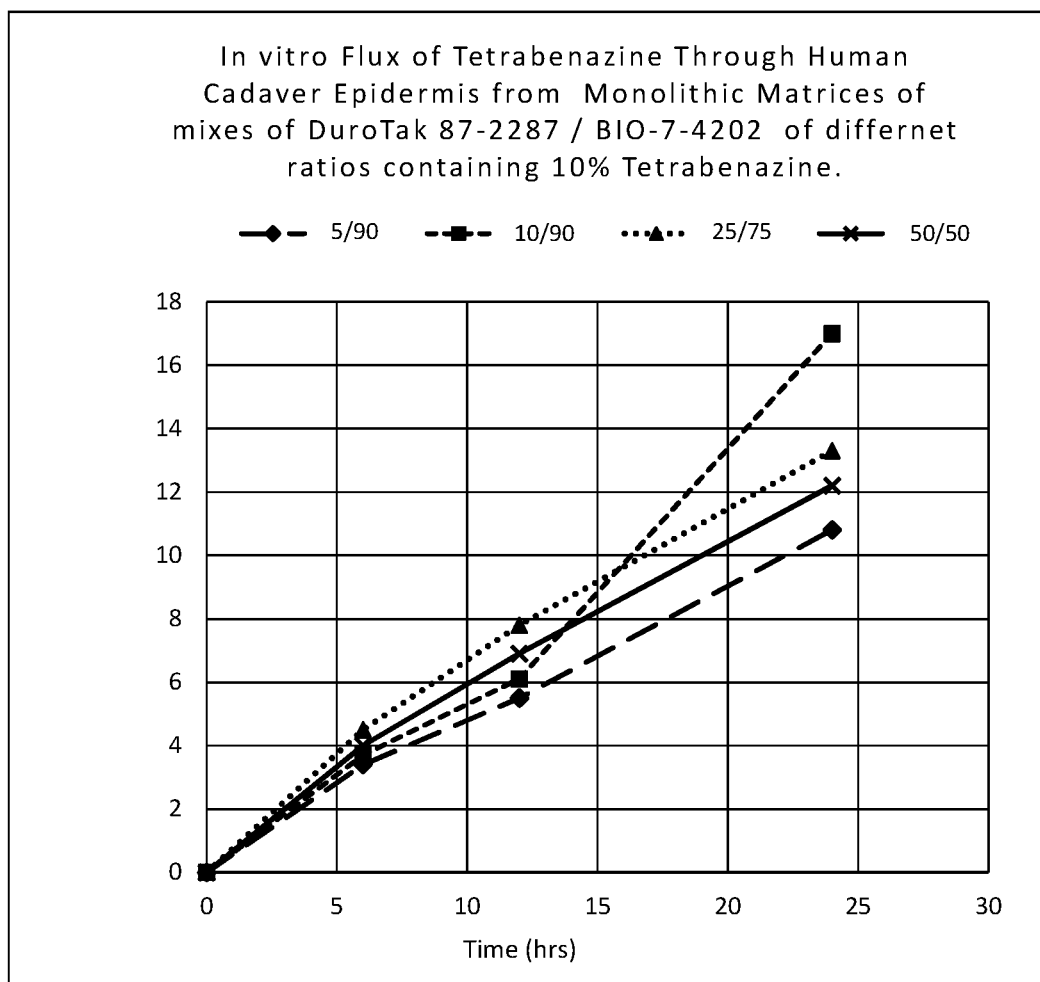

FIG. 2 presents graphs showing the in vitro flux of tetrabenazine through human cadaver epidermis from monolithic matrices of a mixture of Duro-Tak 87-2287 adhesive and BI-7-4202 at different ratios, including 5:95, 10:90, 25:75, and 50:50 (Duro-Tak 87-2287 to BIO-7-4202). All matrices for this figure contain 10% tetrabenazine.

Figure 3:
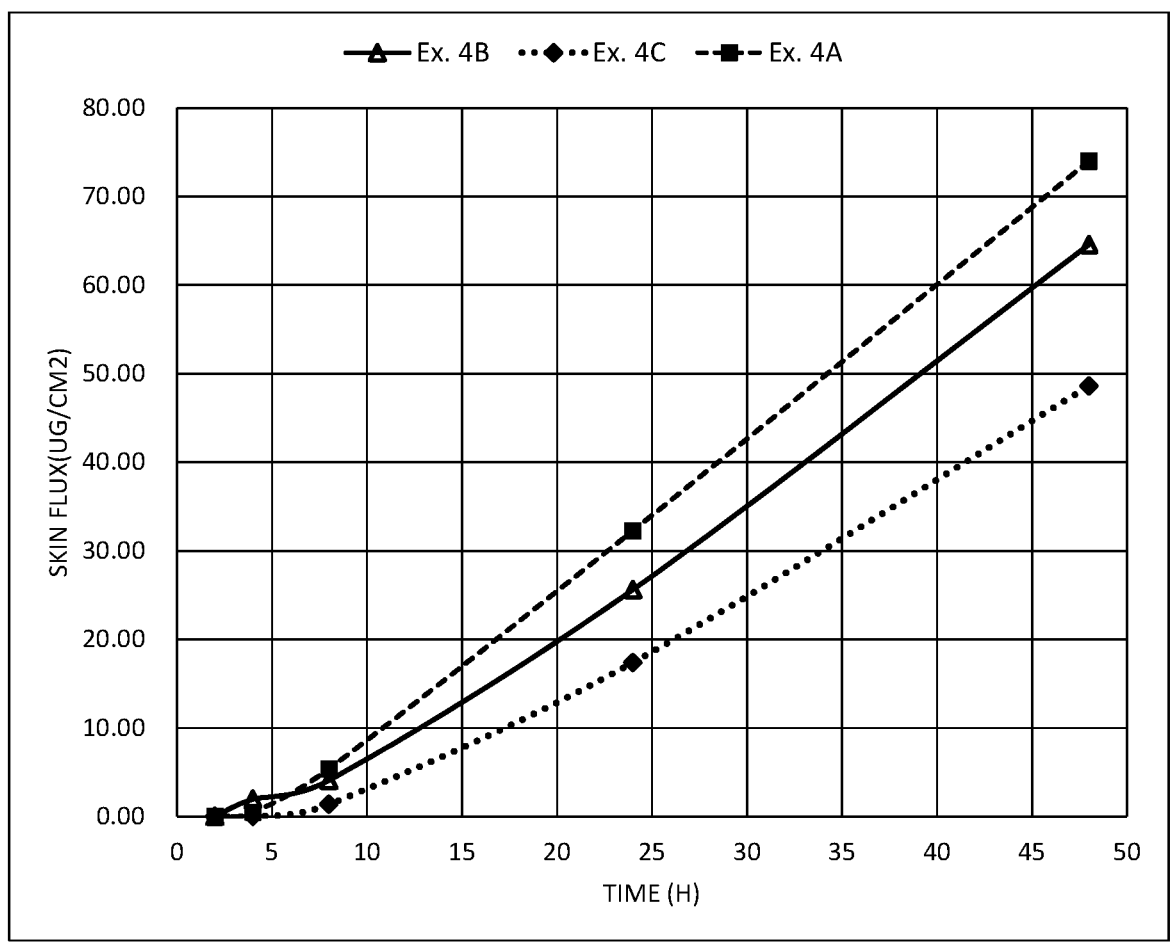

FIG. 3 presents graphs showing in vitro flux of tetrabenazine through human cadaver epidermis from patch formulations prepared using DuroTak 87-900A.

DETAILED DESCRIPTION OF THE INVENTION

In various embodiments, the present invention is directed to pharmaceutical compositions or transdermal delivery devices comprising tetrabenazine and/or a deuterated tetrabenazine (e.g., deutetrabenazine). The pharmaceutical compositions and transdermal delivery devices provide novel options for transdermally delivering tetrabenazine and/or a deuterated tetrabenazine to a subject in need thereof. Tetrabenazine and/or deuterated tetrabenazine have not been previously shown as administrable via the transdermal route. As detailed herein, the inventor has shown that the transdermal delivery device and pharmaceutical compositions disclosed herein (e.g., adhesive compositions herein) can be applied to a subject to achieve a therapeutically relevant flux and therefore can be useful for the treatment of various diseases or disorders such as hyperkinetic movement disorder.

Transdermal delivery of tetrabenazine and/or a deuterated tetrabenazine as described herein can offer many advantages over traditional oral delivery, such as avoiding first-pass metabolism, providing a pharmacokinetic profile with low peak to trough ratio, provides capacity for multiple-day therapy from a single application, avoid food effects on absorption, cease therapy by removing patch if necessary, and easier patient compliance, etc. Further, compared to equal doses of oral administration of tetrabenazine or deutetrabenazine, the transdermal delivery as described herein can decrease inter-individual variation in plasma levels of tetrabenazine or deutetrabenazine or a metabolite thereof and/or can decrease $C_{max}$ (e.g., by 10%, 40%, 60%, or more) of tetrabenazine or deutetrabenazine or a metabolite thereof, for example, without also reducing therapeutic efficacy. Moreover, the transdermal delivery herein can provide similar plasma levels of tetrabenazine or deutetrabenazine or a metabolite thereof when equal doses are administered to subjects who are genotyped based on CYP2D6 expression as poor metabolizer (PM), intermediate metabolizer (IM), or extensive metabolizer (EM). These advantages can ultimately lead to simplified dosing regimen for tetrabenazine and/or a deuterated tetrabenazine (e.g., deutetrabenazine), for example, the need to conduct genotype analysis can be minimized or eliminated, and/or reduced dose-related side effects.

Transdermal Delivery Device Comprising Tetrabenazine

Certain embodiments of the present disclosure are directed to a transdermal delivery device comprising tetrabenazine or a deuterated tetrabenazine (e.g., deutetrabenazine). In some embodiments, the transdermal delivery device comprises a backing layer; a drug layer comprising a drug chosen from tetrabenazine, a deuterated tetrabenazine (e.g., deutetrabenazine), and combinations thereof, and an adhesive layer defining an active surface area. In some embodiments, the drug is in an amount of about 2% to about 30% by weight of the drug layer. In some embodiments, the transdermal delivery device includes a single drug layer. In some embodiments, the transdermal delivery device includes more than one drug layers. In some embodiments, the transdermal delivery device includes a single adhesive layer. In some embodiments, the transdermal delivery device includes more than one adhesive layers.

Various patch designs can be used for the transdermal delivery device herein. For example, in some embodiments, the transdermal delivery device can be a drug-in-adhesive (DIA) patch. In some embodiments, the DIA patch is a single layer patch, wherein the drug layer and the adhesive layer are the same layer, for example, the drug is homogenously dispersed in the adhesive. In some embodiments, the DIA patch is a multilayer patch. For example, two drug-in-adhesive layers can be included in the patch, which is optionally separated by a membrane. In some embodiments, the two DIA layers can have different release characteristics, for example, one of the layers is an immediate release layer whereas the other is a controlled-release layer. In some embodiments, the two DIA layers can have different release characteristics, for example, one of the layers releases the drug relatively fast in a relatively short period of time, whereas the other layer releases the drug for a more sustained period of time.

A drug-in-reservoir (DIR) design can also be used for the transdermal delivery device herein. In some embodiments, the drug layer and the adhesive layer can be two separate layers that are laminated to each other or separated, for example, by a rate-controlling membrane. For example, in some embodiments, the drug layer is a reservoir layer, such as a drug matrix, that is laminated with the adhesive layer.

Other patch designs can also be used for the transdermal delivery device herein. For example, in some embodiments, the transdermal delivery device can be an active patch, such as an iontophoresis patch. In some embodiments, the transdermal delivery device can be a minimally invasive patch, such as a microneedle based patch.

Typically, the transdermal delivery device (e.g., a DIA patch) is supported by an impermeable backing film, and the adhesive surface is protected by a release liner. Various materials can be used as a backing layer for the transdermal delivery device herein. Typically, the backing layer is impermeable. For example, the backing layer can be comprised of impermeable polymeric films such as polyester (PET) or polyethylene (PE) films. In some embodiments, the backing layer can comprise a polyester, such as Scotchpak 9723, Scotchpak 9736 or Scotchpak 1012, a polyurethane film, such as Scotchpak 9701, or a polyethylene film, such as CoTran 9720.

The release liner can be manufactured in the desired size for the present invention. The release liner can be comprised of silicone or fluoro-polymer coated polyester film. The release liner protects the transdermal delivery device during storage and is removed before its use. Silicone-coated release liners include those manufactured by Mylan Corporation, Loparex Corporation, and 3M's Drug Delivery Systems. The fluoro-polymer coated release liners include those manufactured and supplied by 3M's Drug Delivery Systems and Loparex. In some embodiments, the release liner comprises 3M's ScotchPak 9744 or Scotchpak 1022.

The transdermal delivery devices (e.g., DIA patches) herein can have different sizes (patch sizes) depending on its application. Typically, the patch sizes can be about 5 $cm^2$ to about 300 $cm^2$ (e.g., about 5 $cm^2$, about 10 $cm^2$, about 20 $cm^2$, about 30 $cm^2$, about 40 $cm^2$, about 50 $cm^2$, about 60 $cm^2$, about 80 $cm^2$, about 100 $cm^2$, about 120 $cm^2$, about 150 $cm^2$, about 200 $cm^2$ or any ranges between the specified values), for example, about 10 $cm^2$ to about 100 $cm^2$.

When applying the transdermal delivery devices (e.g., DIA patches) herein to a skin of a subject, all of the adhesive surface can become in contact with the skin in theory. Thus, the area of the adhesive surface defines a skin contact area where the active ingredient from the device can permeate the skin, which is also referred herein to as an active surface area. In some embodiments, the adhesive surface is the only surface of the transdermal delivery device that is in contact with the skin upon application, and the active surface area is the same as the area of the adhesive surface. In some embodiments, the adhesive surface and one or more other surfaces of the transdermal delivery device are in contact with the skin upon application, and the entire skin contact area is the active surface area.

The active surface area can determine the doses of the drug to be delivered. Typically, the active surface area can be about 5 $cm^2$ to about 300 $cm^2$ (e.g., about 5 $cm^2$, about 10 $cm^2$, about 20 $cm^2$, about 30 $cm^2$, about 40 $cm^2$, about 50 $cm^2$, about 60 $cm^2$, about 80 $cm^2$, about 100 $cm^2$, about 120 $cm^2$, about 150 $cm^2$, about 200 $cm^2$ or any ranges between the specified values), for example, about 10 $cm^2$ to about 100 $cm^2$.

The Drug Layer

Typically, the drug layer comprises tetrabenazine, deuterated tetrabenazine, or a combination thereof. In some embodiments, the drug layer can optionally include one or more other ingredients, for example, selected from skin permeation enhancers, humectants, plasticizers, antioxidants, anti-irritants, gel-forming agents, drug release modifiers, solvents, crystallization inhibitors, and additional active ingredients. In some embodiments, the drug layer is adjusted such that the transdermal delivery device achieves the skin flux characteristics described herein. It should be noted that the pharmaceutical compositions used for the drug layer herein can also be a novel formulation, independent of the transdermal delivery device and/or the skin flux characteristics herein. Thus, some embodiments of the present disclosure are also directed to such pharmaceutical compositions.

In some embodiments, the drug in the drug layer can be tetrabenazine. The tetrabenazine in the transdermal delivery device described herein is not limited to a particular enantiomer and can be in a racemic form, a substantially pure R,R-tetrabenazine (e.g., with less than 10%, less than 5%, less than 1%, or less than 0.1% of the S,S-isomer), a substantially pure S,S-tetrabenazine (e.g., with less than 10%, less than 5%, less than 1%, or less than 0.1% of the R,R-isomer), or a mixture of R,R-tetrabenazine and S,S-tetrabenazine in any ratio. In some embodiments, the tetrabenazine in the transdermal delivery device is in racemic form. In some embodiments, the tetrabenazine in the transdermal delivery device is a substantially pure R,R-tetrabenazine. In some embodiments, tetrabenazine is the only drug in the drug layer. In some embodiments, tetrabenazine is the only drug in the transdermal delivery device. In some embodiments, the drug layer and/or the transdermal delivery device can also include other active ingredients.

In some embodiments, the drug in the drug layer can be a deuterated tetrabenazine. As used herein, a deuterated tetrabenazine refers to a compound resulted from substituting one or more hydrogen atoms of tetrabenazine with deuterium such that each substituted position has a deuterium content above the natural abundance, i.e., the substituted position is enriched with deuterium. In some embodiments, the deuterated tetrabenazine has at least one position with deuterium enriched to greater than 10% deuterium, greater than 50% deuterium, greater than 90% deuterium, greater than 95% deuterium or greater than 98% deuterium. A preferred example of deuterated tetrabenazine is deutetrabenazine, the racemic form of which is the active ingredient in Austedo™ tablets. The deuterated tetrabenazine in the transdermal delivery device described herein is not limited to a particular enantiomer and can be in a racemic form, a substantially pure R,R-isomer, e.g., R,R-deutetrabenazine (see below), (e.g., with less than 10%, less than 5%, less than 1%, or less than 0.1% of the S,S-isomer), a substantially pure S,S-isomer, e.g., S,S-deutetrabenazine (see below), (e.g., with less than 10%, less than 5%, less than 1%, or less than 0.1% of the R,R-isomer), or a mixture of R,R-isomer and S,S-isomer in any ratio. In some embodiments, the transdermal delivery device comprises deutetrabenazine in racemic form. In some embodiments, the transdermal delivery device comprises deutetrabenazine as a substantially pure R,R-deutetrabenazine. In some embodiments, deutetrabenazine is the only drug in the drug layer. In some embodiments, deutetrabenazine is the only drug in the transdermal delivery device. In some embodiments, the drug layer and/or the transdermal delivery device can also include other active ingredients.

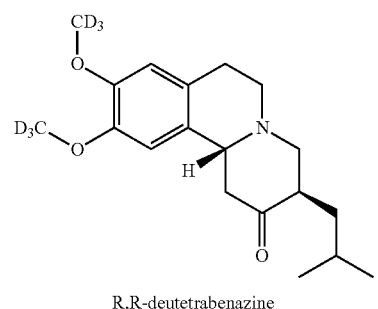

R,R-deutetrabenazine

-continued

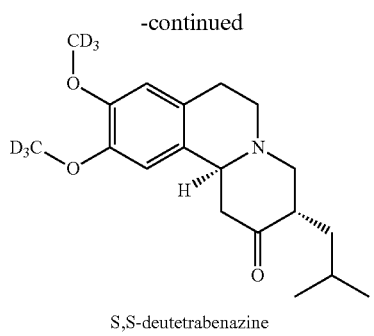

S,S-deutetrabenazine

The drug can be present in the drug layer of the transdermal delivery device in various amounts. In some embodiments, the drug layer comprises tetrabenazine, deuterated tetrabenazine, or a combination thereof, in an amount of about 2% to about 30% (e.g., about 2%, about 2.5%, about 5%, about 8%, about 10%, about 15%, about 18%, about 20%, about 25%, about 30%, or any ranges in between the recited values) by weight of the drug layer. In some specific embodiments, the drug layer comprises tetrabenazine, deuterated tetrabenazine, or a combination thereof, in the amount of about 2%, about 2.5%, about 5%, about 8%, about 10%, about 15%, or about 20% by weight of the drug layer. In some embodiments, tetrabenazine, deuterated tetrabenazine, or a combination thereof, only exists in the drug layer (e.g., in a drug-in-adhesive layer) of the transdermal delivery device.

The weight and thickness of the drug layer can vary depending on different factors such as drug concentration and desired duration of administration, etc. The drug layer is typically designed for application (e.g., delivering tetrabenazine or deutetrabenazine) for a period of time selected from about 8 hours, about 12 hours, about 18 hours, about 24 hours, about 2 days, about 3 days, about 4 days, about 5 days, about 6 days, and about 7 days. In some embodiments, the drug layer can have a coat weight of about 0.01 g/cm$^2$ to about 5 g/cm$^2$, e.g., about 0.05 g/cm$^2$ to about 5 g/cm$^2$, about 0.1 g/cm$^2$ to about 5 g/cm$^2$, such as about 0.05 g/cm$^2$ to about 0.90 g/cm$^2$, about 0.1 g/cm$^2$ to about 0.90 g/cm$^2$ (e.g., about 0.1 g/cm$^2$ to about 0.5 g/cm$^2$) active surface area. In some embodiments, the drug layer can have a thickness of about 1.5 mm to about 10 mm, such as about 1.5 mm to about 3.5 mm (e.g., about 2 mm to about 3.5 mm). In some embodiments, the drug layer can have a thickness of about 0.1 mil to about 100 mil, such as about 1 mil to about 50 mil (e.g., about 1 mil to about 10 mil, or about 1.5 mil to about 3.5 mil).

Skin permeation enhancers can enhance the skin permeability of tetrabenazine or deuterated tetrabenazine through the skin and can be optionally included in the drug layer. In some embodiments, the drug layer is free or substantially free of a permeation enhancer. However, in some embodiments, various skin permeation enhancers can be included. Non-limiting useful skin permeation enhancers include, for example, sulfoxides (e.g., dimethylsulfoxide, DMSO), Azones (e.g., laurocapram), pyrrolidones (e.g., 2-pyrrolidone, 2P), alcohols and alkanols (e.g., ethanol or decanol), esters, glycols (e.g., propylene glycol (PG)), surfactants (e.g., Tween 80), terpenes, and combinations thereof. See, e.g., Williams et al., Adv Drug Deliv Rev. 27; 56(5):603-18 (2004). In some embodiments, the permeation enhancer comprises one or more compounds chosen from sulfoxides, alcohols, alkanols, esters, glycols, and surfactants. In some embodiments, the permeation enhancer comprises one or more compounds chosen from dimethyl sulfoxide (DMSO), oleic alcohol, oleayl oleate, oleic acid, levulinic acid, other fatty acids and fatty-acid esters, propylene glycol, dipropylene glycol, ethanol, and surfactants such as Tween 80. The skin permeation enhancer is typically included in the amount of about 1% to about 25% by weight of the pharmaceutical composition, for example, about 2%, about 5%, about 10%, about 15%, about 20%, about 25%, or any ranges between the specified values, by weight of the pharmaceutical composition.

Other suitable excipients useful in the preparation of transdermal delivery devices such as humectants, plasticizers, antioxidants, anti-irritants, gel-forming agents, crystallization inhibitors, drug release modifiers etc. can also be included in the drug layer (e.g., a drug-in-adhesive layer) or otherwise in the transdermal delivery device herein. In some embodiments, additional active ingredient(s) can also be included in the drug layer or otherwise in the transdermal delivery device herein. These excipients are within the knowledge of those skilled in the art, and can be found, for example, in the Handbook of Pharmaceutical Excipients, (7$^{th}$ ed. 2012), the entire content of which is hereby incorporated by reference.

The Adhesive Layer

The adhesive layer can be the same or a separate layer from the drug layer. In a typical DIA patch, the drug is homogeneously dispersed in an adhesive to form a drug-in-adhesive layer. Other designs, such as a DIR patch, can also include an adhesive layer separate from the drug layer, for example, by a membrane. In some embodiments, more than one adhesive layers (e.g., two or more drug-in-adhesive layers) can be used in the transdermal delivery device.

The adhesive layer typically includes a pressure sensitive adhesive (PSA). PSAs are generally known in the art. See, e.g., Tan et al., Pharm Sci & Tech Today, 2:60-69 (1999). Non-limiting useful PSAs include polyisobutylenes (PIB), silicone polymers, acrylate copolymers, and combinations thereof. In some embodiments, the pressure sensitive adhesive comprises a polyisobutylene adhesive, a silicone polymer adhesive, an acrylate copolymer adhesive, or a combination thereof. In some embodiments, the pressure sensitive adhesive comprises an acrylate copolymer adhesive. Non-limiting useful acrylate copolymers include, for example, acrylic pressure sensitive adhesives such as a poly acrylate vinyl acetate copolymer, e.g., Duro-Tak 87-2287, Duro-Tak 87-4098, Duro-Tak 87-4287, or Duro-Tak 87-2516, Duro-Tak 87-2852 or Duro-Tak 87-2194), which are manufactured by Henkel Adhesives. In some embodiments, the pressure sensitive adhesive can be a non-reactive acrylate adhesive (e.g., as described herein, such as Duro-Tak 87-900A), for example, an acrylate adhesive that has no functional groups containing reactive hydrogen moieties, or an acrylate adhesive that has no functional groups selected from epoxy, —OH, —COOH, and combinations thereof. PIBs are elastomeric polymers that are commonly used in PSAs, both as primary-base polymers and as tackifiers. PIBs are homopolymers of isobutylene and feature a regular structure of a carbon-hydrogen backbone with only terminal unsaturation. Non-limiting useful PIBs include those marketed under the trade name Oppanol by BASF. However, in some embodiments, the pressure sensitive adhesive does not contain a PIB based adhesive. The silicone polymers are a high molecular weight polydimethylsiloxane that contains residual silanol functionality (SiOH) on the ends of the polymer chains. Non-limiting useful silicone PSAs for use in pharmaceutical applications include those available from Dow Corning Corporation, for example under the trade name of BIO-PSA, e.g., BIO-7-4202. In some embodiments, the adhesive layer is about 1.5 mils to about 10 mils (e.g., about 1.5 mils to about 2 mils) thick.

One or more adhesives can be used in the adhesive layer. For example, in some embodiments, the adhesive layer can include a mixture of an acrylate copolymer adhesive (e.g., Durotak 87-2287) and a silicone adhesive (e.g., BIO-7-4202) in various ratios (e.g., a ration of acrylate adhesive to silicone adhesive ranging from about 1:10 to about 10:1). As detailed in the Examples section, varying the adhesive components can affect the flux characteristics of the transdermal delivery device.

The adhesive layer is typically formulated such that the transdermal delivery device can adhere to the skin of a user for a desired period of time. For example, in some embodiments, the transdermal delivery device is capable of adhering continuously to the skin of a user for about 8 hours, about 12 hours, about 18 hours, about 24 hours, about 2 days, about 3 days, about 4 days, about 5 days, about 6 days, or about 7 days or more.

The Adhesive Composition

In some embodiments, the present invention also provides an adhesive composition comprising a drug chosen from tetrabenazine, deuterated tetrabenazine (e.g., deutetrabenazine), and combinations thereof in an adhesive. In some embodiments, the drug is homogenously dispersed in the adhesive. Suitable drug and adhesives include any of those described herein.

In some embodiments, the adhesive composition is capable of adhering continuously to the skin of a user for an extended period of time selected from about 8 hours, about 12 hours, about 18 hours, about 24 hours, about 2 days, about 3 days, about 4 days, about 5 days, about 6 days, or about 7 days or more.

In some embodiments, the adhesive is a pressure sensitive adhesive. In some embodiments, the pressure sensitive adhesive comprises a polyisobutylene (PIB) adhesive, a silicone polymer adhesive, an acrylate copolymer adhesive, or a combination thereof. In some embodiments, the pressure sensitive adhesive can be a non-reactive acrylate adhesive (e.g., as described herein, such as Duro-Tak 87-900A), for example, an acrylate adhesive that has no functional groups containing reactive hydrogen moieties, or an acrylate adhesive that has no functional groups selected from epoxy, —OH, —COOH, and combinations thereof. In some embodiments, the pressure sensitive adhesive does not include a polyisobutylene (PIB) adhesive and/or a silicone polymer adhesive.

The drug in the adhesive composition is preferably tetrabenazine or deutetrabenazine. In some embodiments, the drug is tetrabenazine. In some embodiments, the tetrabenazine is a substantially pure R,R-tetrabenazine. In some embodiments, the drug is deutetrabenazine. In some embodiments, the deutetrabenazine is a substantially pure R,R-deutetrabenazine. In some embodiments, tetrabenazine is the only active ingredient in the adhesive composition. In some embodiments, deutetrabenazine is the only active ingredient in the adhesive composition. In some embodiments, the tetrabenazine or deutetrabenazine is present in an amount of about 2% to about 30% (e.g., about 2%, about 2.5%, about 5%, about 8%, about 10%, about 15%, about 18%, about 20%, about 25%, about 30%, or any ranges in between the recited values) by weight of the adhesive composition. In some specific embodiments, the adhesive composition comprises tetrabenazine or deutetrabenazine in the amount of about 2%, about 2.5%, about 5%, about 8%, about 10%, about 15%, or about 20% by weight of the adhesive composition. In some embodiments, the active ingredient is present in an amount of about 2% to about 7% by weight.

In some embodiments, the adhesive composition further comprises a permeation enhancer. Suitable permeation enhancers include any of those described herein. In some embodiments, the adhesive composition is free of a permeation enhancer. In some embodiments, the adhesive composition is free of isopropyl myristate.

In some embodiments, the adhesive composition can optionally include one or more ingredients selected from humectants, plasticizers, antioxidants, anti-irritants, gel-forming agents, crystallization inhibitors, drug release modifiers, and additional active ingredients. For example, in some embodiments, the adhesive composition can comprise an antioxidant, e.g., a gallate antioxidant, such as propyl gallate. In some embodiments, the adhesive composition can comprise a crystallization inhibitor, such as a polyvinylpyrrolidone polymer, a cross-linked polyvinylpyrrolidone polymer, a polyvinylpyrrolidone copolymer, a cellulose based polymer, a polycarboxylic acid polymer, a polymethacrylate, a polyethylene glycol, polyvinyl acetate and polyvinylcaprolactame-based graft copolymer (PVAc-PVCap-PEG), or a combination thereof. In some preferred embodiments, the adhesive composition comprises a crystallization inhibitor which is a copolymer of butyl methacrylate and methyl methacrylate. In some embodiments, the adhesive composition comprises a crystallization inhibitor which is a polyethylene glycol, polyvinyl acetate and polyvinylcaprolactame-based graft copolymer.

The adhesive composition can be included in a transdermal delivery device. Typically, such transdermal delivery device also includes a backing layer and a release liner which protects the adhesive surface prior to use. In some embodiments, the adhesive composition can be included as the drug layer in any one of the transdermal delivery device described herein.

Skin Flux Characteristics

The transdermal delivery device described herein preferably provides certain desired skin flux characteristics. Typically, the transdermal delivery device can deliver to a subject in need thereof about 0.1 mg/day/cm$^2$ to about 5 mg/day/cm$^2$ (e.g., about 0.1 mg/day/cm$^2$, about 0.2 mg/day/cm$^2$, about 0.5 mg/day/cm$^2$, about 1 mg/day/cm$^2$, about 2 mg/day/cm$^2$, about 5 mg/day/cm$^2$, or any ranges between the specified values) of the drug (e.g., tetrabenazine or deutetrabenazine), for example, over a period of time selected from about 8 hours, about 12 hours, about 18 hours, about 24 hours, about 2 days, about 3 days, about 4 days, about 5 days, about 6 days, and about 7 days. However, in some embodiments, the transdermal delivery device can deliver more than about 5 mg/day/cm$^2$, for example, about 8 mg/day/cm$^2$, about 10 mg/day/cm$^2$, about 15 mg/day/cm$^2$, about 20 mg/day/cm$^2$, or any ranges between the recited values, of the drug (e.g., tetrabenazine or deutetrabenazine). In some embodiments, the transdermal delivery device can deliver less than about 0.1 mg/day/cm$^2$, such as about 0.01 mg/day/cm$^2$, about 0.02 mg/day/cm$^2$, about 0.05 mg/day/cm$^2$, about 0.1 mg/day/cm$^2$, or any ranges between the recited values, of the drug (e.g., tetrabenazine or deutetrabenazine).

In some embodiments, the transdermal delivery device can deliver to a subject in need thereof about 0.1 mg/day/cm$^2$ to about 1 mg/day/cm$^2$ (e.g., about 0.1 mg/day/cm$^2$, about 0.2 mg/day/cm$^2$, about 0.5 mg/day/cm$^2$, about 1 mg/day/cm$^2$, or any ranges between the specified values) of the drug (e.g., tetrabenazine or deutetrabenazine), for example, over a period of time selected from about 24 hours, about 2 days, about 3 days, about 4 days, about 5 days, about 6 days, and about 7 days. In some embodiments, the transdermal delivery device can deliver about 0.1 mg/day/cm² to about 5 mg/day/cm² (e.g., about 0.1 mg/day/cm², about 0.2 mg/day/cm², about 0.5 mg/day/cm², about 1 mg/day/cm², about 5 mg/day/cm², or any ranges between the specified values) of the drug (e.g., tetrabenazine or deutetrabenazine), for example, over a period of time over a period of more than 7 days. In some embodiments, the transdermal delivery device can also deliver about 0.1 mg/day/cm² to about 5 mg/day/cm² (e.g., about 0.1 mg/day/cm², about 0.2 mg/day/cm², about 0.5 mg/day/cm², about 1 mg/day/cm², or any ranges between the specified values) of the drug (e.g., tetrabenazine or deutetrabenazine), for example, over a period of time less than 24 hours such as less than 18 hours, less than 12 hours, less than 8 hours, or less than 4 hours.

In some embodiments, the transdermal delivery device comprises tetrabenazine, and the transdermal delivery device provides one or more of the following skin flux characteristics when tested in vitro using human cadaver skin: a) a cumulative tetrabenazine permeated of about 0.1 µg/cm² to about 150 µg/cm² (e.g., about 0.1 µg/cm², about 0.5 µg/cm², about 1 µg/cm², about 5 g/cm², about 10 µg/cm², about 15 µg/cm², about 20 µg/cm², about 50 µg/cm², about 75 µg/cm², about 100 µg/cm², about 125 µg/cm², about 150 µg/cm², or any ranges between the recited values) at 6 hours post administration based on the active surface area; b) a cumulative tetrabenazine permeated of about 2 g/cm² to about 400 µg/cm² (e.g., about 2 g/cm², about 5 g/cm², about 10 µg/cm², about 15 µg/cm², about 20 µg/cm², about 50 µg/cm², about 100 µg/cm², about 200 µg/cm², about 300 µg/cm², about 400 µg/cm², or any ranges between the recited values) at 12 hours post administration based on the active surface area; and c) a cumulative tetrabenazine permeated of about 5 g/cm² to about 1000 µg/cm² (e.g., about 5 g/cm², about 10 µg/cm², about 15 µg/cm², about 20 µg/cm², about g/cm², about 50 µg/cm², about 100 µg/cm², about 200 µg/cm², about 300 µg/cm², about 400 µg/cm², about 600 µg/cm², about 800 µg/cm², about 1000 µg/cm², or any ranges between the recited values) at 24 hours post administration based on the active surface area. In some embodiments, the tetrabenazine is present in an amount of about 2% to about 30% (e.g., about 2% to about 20%, about 2% to about 10%, about 2% to about 5%, about 5% to about 10%, about 10% to about 15%) by weight of the drug layer. In some embodiments, the tetrabenazine is present in an amount of about 2%, about 5%, about 8%, about 10%, about 15%, about 20%, or any ranges between the recited value, by weight of the drug layer. In some embodiments, the tetrabenazine is a substantially pure R,R-tetrabenazine.

In some embodiments, the tetrabenazine is present in an amount of about 2% to about 5% by weight of the drug layer, and the transdermal delivery device provides one or more of the following skin flux characteristics when tested in vitro using human cadaver skin: a) a cumulative tetrabenazine permeated of about 0.1 µg/cm² to about 100 µg/cm² (e.g., about 0.1 µg/cm², about 0.5 µg/cm², about 1 µg/cm², about 5 µg/cm², about 10 µg/cm², about 15 µg/cm², about 20 µg/cm², about 50 µg/cm², about 75 µg/cm², about 100 µg/cm², or any ranges between the recited values) at 6 hours post administration based on the active surface area; b) a cumulative tetrabenazine permeated of about 2 g/cm² to about 200 µg/cm² (e.g., about 2 µg/cm², about 5 µg/cm², about 10 µg/cm², about 15 µg/cm², about 20 µg/cm², about 50 µg/cm², about 100 µg/cm², about 200 µg/cm², or any ranges between the recited values) at 12 hours post administration based on the active surface area; and c) a cumulative tetrabenazine permeated of about 5 g/cm² to about 600 µg/cm² (e.g., about 5 µg/cm², about 10 µg/cm², about 15 µg/cm², about 20 µg/cm², about 25 µg/cm², about 50 µg/cm², about 100 µg/cm², about 200 µg/cm², about 300 µg/cm², about 400 µg/cm², about 600 µg/cm², or any ranges between the recited values) at 24 hours post administration based on the active surface area.

In some embodiments, the tetrabenazine is present in an amount of about 5% to about 10% by weight of the drug layer, and the transdermal delivery device provides one or more of the following skin flux characteristics when tested in vitro using human cadaver skin: a) a cumulative tetrabenazine permeated of about 0.5 µg/cm² to about 150 µg/cm² (e.g., about 1 µg/cm², about 5 µg/cm², about 10 µg/cm², about 15 µg/cm², about 20 µg/cm², about 50 µg/cm², about 75 µg/cm², about 100 µg/cm², about 150 µg/cm², or any ranges between the recited values) at 6 hours post administration based on the active surface area; b) a cumulative tetrabenazine permeated of about 4 g/cm² to about 400 µg/cm² (e.g., about 4 µg/cm², about 6 µg/cm², about 10 µg/cm², about 15 µg/cm², about 20 µg/cm², about 50 µg/cm², about 100 µg/cm², about 200 µg/cm², about 400 µg/cm², or any ranges between the recited values) at 12 hours post administration based on the active surface area; and c) a cumulative tetrabenazine permeated of about 6 g/cm² to about 1000 µg/cm² (e.g., about 6 µg/cm², about 10 µg/cm², about 15 µg/cm², about 20 µg/cm², about 25 µg/cm², about 50 µg/cm², about 100 µg/cm², about 200 µg/cm², about 300 µg/cm², about 400 µg/cm², about 600 µg/cm², about 1000 µg/cm², or any ranges between the recited values) at 24 hours post administration based on the active surface area.

In some embodiments, the tetrabenazine is present in an amount of about 10% to about 15% by weight of the drug layer, and the transdermal delivery device provides one or more of the following skin flux characteristics when tested in vitro using human cadaver skin: a) a cumulative tetrabenazine permeated of about 0.5 µg/cm² to about 150 µg/cm² (e.g., about 1 µg/cm², about 2 µg/cm², about 5 µg/cm², about 10 µg/cm², about 15 µg/cm², about 20 µg/cm², about 50 µg/cm², about 75 µg/cm², about 100 µg/cm², about 150 µg/cm², or any ranges between the recited values) at 6 hours post administration based on the active surface area; b) a cumulative tetrabenazine permeated of about 4 g/cm² to about 400 µg/cm² (e.g., about 4 µg/cm², about 6 µg/cm², about 10 µg/cm², about 15 µg/cm², about 20 µg/cm², about g/cm², about 40 µg/cm², about 50 µg/cm², about 100 µg/cm², about 200 µg/cm², about 400 µg/cm², or any ranges between the recited values) at 12 hours post administration based on the active surface area; and c) a cumulative tetrabenazine permeated of about 8 g/cm² to about 1000 µg/cm² (e.g., about 8 g/cm², about 10 µg/cm², about 15 µg/cm², about 20 µg/cm², about 30 µg/cm², about 40 µg/cm², about 50 µg/cm², about 60 µg/cm², about 100 µg/cm², about 200 µg/cm², about 300 µg/cm², about 400 µg/cm², about 600 µg/cm², about 1000 µg/cm², or any ranges between the recited values) at 24 hours post administration based on the active surface area.

In some embodiments, the transdermal delivery device comprises a deuterated tetrabenazine (e.g., deutetrabenazine), and the transdermal delivery device provides one or more of the following skin flux characteristics when tested in vitro using human cadaver skin: a) a cumulative deuterated tetrabenazine permeated of about 0.1 µg/cm² to about 150 µg/cm² (e.g., about 0.1 µg/cm², about 0.5 µg/cm², about 1 µg/cm², about 5 µg/cm², about g/cm², about 15

µg/cm², about 20 µg/cm², about 50 µg/cm², about 75 µg/cm², about 100 µg/cm², about 125 µg/cm², about 150 µg/cm², or any ranges between the recited values) at 6 hours post administration based on the active surface area; b) a cumulative deuterated tetrabenazine permeated of about 2 g/cm² to about 400 µg/cm² (e.g., about 2 µg/cm², about 5 g/cm², about 10 µg/cm², about 15 µg/cm², about 20 µg/cm², about 50 µg/cm², about 100 µg/cm², about 200 µg/cm², about 300 µg/cm², about 400 µg/cm², or any ranges between the recited values) at 12 hours post administration based on the active surface area; and c) a cumulative deuterated tetrabenazine permeated of about 5 g/cm² to about 1000 µg/cm² (e.g., about 5 µg/cm², about 10 µg/cm², about 15 µg/cm², about 20 µg/cm², about g/cm², about 50 µg/cm², about 100 µg/cm², about 200 µg/cm², about 300 µg/cm², about 400 µg/cm², about 600 µg/cm², about 800 µg/cm², about 1000 µg/cm², or any ranges between the recited values) at 24 hours post administration based on the active surface area. In some embodiments, the deuterated tetrabenazine is present in an amount of about 2% to about 30% (e.g., about 2% to about 20%, about 2% to about 10%, about 2% to about 5%, about 5% to about 10%, about 10% to about 15%) by weight of the drug layer. In some embodiments, the deuterated tetrabenazine is present in an amount of about 2%, about 5%, about 8%, about 10%, about 15%, about 20%, or any ranges between the recited value, by weight of the drug layer. In some embodiments, the deuterated tetrabenazine is a substantially pure R,R-deutetrabenazine.

Transdermal delivery devices with the above flux characteristics can be prepared by those skilled in the art in view of the present disclosure. Preparations of a few transdermal delivery devices are also exemplified in the Examples section. The cumulative drug (tetrabenazine, deuterated tetrabenazine, or a combination thereof) permeated can be adjusted, for example, by varying the composition of the drug layer (e.g., drug concentration, permeation enhancer, coat weight, types of adhesives etc.).

Compositions Containing Non-Reactive Adhesives

Compositions using non-reactive adhesives can provide certain advantages. As illustrated in the Examples section, tetrabenazine formulations with non-reactive adhesives can be more stable compared to corresponding formulations with adhesives having functional groups. For example, when a non-reactive adhesive DuroTak 87-900A was used as a matrix polymer, which is understood to be a copolymer of 2-EHA (2-ethyl hexyl acrylate) (about 45 wt % based on monomer composition), MA (methyl acrylate) (about 35 wt % based on monomer composition) and t-OA (tert octyl acrylamide) (about 20 wt % based on monomer composition), the resulted tetrabenazine adhesive composition was found to be stable after shelf storage for 4 weeks at 40° C., with no drug crystals observed and no drug degradations. In contrast, tetrabenazine adhesive composition formed using a more common adhesive matrix polymer, DuroTak 87-2287 (containing epoxy and hydroxyl functional groups), or Duro-Tak 87-2677 (containing carboxylic acid functional groups), the resulted formulation showed yellowish color after shelf storage for 4 weeks at 40° C., indicating instability of the active ingredient due to oxidation and/or other degradation.

In some embodiments, the present invention provides an adhesive composition comprising an active ingredient (or alternatively referred to as "drug") dispersed (e.g., homogenously dispersed or dissolved) in a non-reactive acrylate pressure sensitive adhesive, wherein the active ingredient is selected from tetrabenazine, deuterated tetrabenazine, or a combination thereof. Unless otherwise obvious from context, in any of the embodiments described herein, the active ingredient can exist predominantly (e.g., at least 80%, at least 90%, or at least 95% by weight) in its free base form, for example, as tetrabenazine base, deutetrabenazine base, etc. The non-reactive acrylate pressure sensitive adhesive is typically present in an amount of about 50% to about 97% (e.g., about 50%, about 60%, about 65%, about 70%, about 75%, about 80%, about 85%, about 90%, about 95%, about 97%, or any ranges between the recited values) by weight of the adhesive composition.

Non-reactive acrylate pressure sensitive adhesives useful for embodiments of the present disclosure include those sold by Henkel, for example, under the product name DuroTak 87-900A. U.S. Pat. No. 9,056,060, the contents of which is herein incorporated by reference in its entirety, also describes non-reactive acrylate pressure sensitive adhesives, which can be used for embodiments of the present disclosure.

In some embodiments, the non-reactive acrylate pressure sensitive adhesive does not have functional groups containing reactive hydrogen moieties. In some embodiments, the non-reactive acrylate pressure sensitive adhesive does not have functional groups selected from epoxy, —OH, —COOH, and combinations thereof. For example, in some embodiments, the non-reactive acrylate pressure sensitive adhesive is a copolymer of alkyl acrylate without functional groups containing reactive hydrogen moieties or without functional groups selected from epoxy, —OH, —COOH, and combinations thereof. In some embodiments, the non-reactive acrylate pressure sensitive adhesive can be a copolymer of monomers comprising, consisting essentially of, or consisting of alkyl acrylates. For example, in some embodiments, the non-reactive acrylate pressure sensitive adhesive can be a copolymer derived from monomers consisting of alkyl acrylates, e.g., a copolymer derived from a monomer of $C_2$-$C_{18}$ alkyl acrylate (preferably $C_4$-$C_{10}$ branched or straight-chain alkyl acrylate) and a monomer of methyl acrylate, more preferably, a copolymer derived from a monomer of hexylethyl acrylate (e.g., 2-ethyl hexyl acrylate) and a monomer of methyl acrylate. In some embodiments, the copolymer of alkyl acrylate is a copolymer of hexylethyl acrylate (e.g., 2-ethyl hexyl acrylate) and methyl acrylate, and optionally other monomer(s) with no functional groups containing reactive hydrogen moieties, such as —OH, —COOH groups. In some embodiments, the non-reactive acrylate pressure sensitive adhesive can be a copolymer derived from monomers including alkyl acrylates and other monomers with no functional groups containing reactive hydrogen moieties, such as —OH, —COOH groups. For example, in some embodiments, the non-reactive acrylate pressure sensitive adhesive can be a copolymer derived from a monomer of hexylethyl acrylate (e.g., 2-ethyl hexyl acrylate), a monomer of methyl acrylate, and one or more monomers with no functional groups containing reactive hydrogen moieties, such as —OH, —COOH groups, such as acrylamide monomers (e.g., tert octyl acrylamide, dimethyl acrylamide, isopropyl acrylamide, or vinyl acetamide). As used herein, amide NH or amide $NH_2$ groups should not be considered as reactive hydrogen moieties. In some embodiments, the non-reactive acrylate pressure sensitive adhesive can be a copolymer derived from a monomer of $C_2$-$C_{18}$ alkyl acrylate (preferably $C_4$-$C_{10}$ branched or straight-chain alkyl acrylate), a monomer of methyl acrylate, and one or more acrylamide monomers (e.g., tert octyl acrylamide) with no functional groups selected from epoxy, —OH, —COOH groups, and combinations thereof. The weight percentages of the monomers can vary, for example, in some embodiments, the percentage of the monomers of the non-reactive acrylate pressure sensitive adhesive can be the following: the percentage of the monomer of $C_2$-$C_{18}$ alkyl acrylate (preferably $C_4$-$C_{10}$ branched or straight-chain alkyl acrylate, such as 2-ethylhexyl acrylate) can be at about 45 wt %, the percentage of the monomer of methyl acrylate can be at about 35 wt %, and the percentage of the monomer of the one or more acrylamide monomers (e.g., tert octyl acrylamide) can be at about 20 wt %.

The non-reactive acrylate pressure sensitive adhesive typically does not include vinyl acetate. The non-reactive acrylate pressure sensitive adhesive typically also does not include a crosslinker. The non-reactive acrylate pressure sensitive adhesive typically can have various viscosities. In some embodiments, the non-reactive acrylate pressure sensitive adhesive can have a viscosity of about 1,500 cP to about 20,000 cP, more preferably, about 1,500 cP to about 10,000 cP, such as about 1,800 cP, about 5,000 cP, about 10,000 cP, or ranges between the recited values. In some embodiments, the non-reactive acrylate pressure sensitive adhesive can be selected such that adhesive composition can adhere continuously to the skin of a user for about 8 hours, about 12 hours, about 18 hours, about 24 hours, about 2 days, about 3 days, about 4 days, about 5 days, about 6 days, or about 7 days or more.

In some formulations, addition of a permeation enhance can cause significant degradations of the active ingredient (e.g., tetrabenazine) in the patch formulation. Thus, in some embodiments, the adhesive composition can be free or substantially free of a permeation enhancer. For example, in some embodiments, the adhesive composition herein can be free of a permeation enhancer. In some embodiments, the adhesive composition herein can be free of a permeation enhance selected from fatty alcohols, fatty acids, fatty esters and combinations thereof. In some embodiments, the adhesive composition herein can be free of isopropyl myristate. However, it should be understood that in some cases, permeation enhancers can be added to the adhesive compositions, for example, in an amount that does not cause significant degradation of the active ingredient.

Antioxidants are typically included in the adhesive composition herein. For example, antioxidants can be added to reduce the extent of degradation of the active ingredient. However, unexpectedly, it was found that some antioxidants work better than others in protecting tetrabenazine from degradation. For example, adhesive compositions containing a gallate antioxidant (e.g., propyl gallate in the examples) were found to be shelf stable. In any of the embodiments herein, shelf stable, storage stable, or stable after shelf storage, and the like, can mean that a tested device or composition, after shelf storage at 40 □ for 4 weeks, (1) HPLC analysis shows that the tested device or composition is free or substantially free (e.g., less than 1%, less than 0.5%, less than 0.05%, or not detected by HPLC) of one or more (preferably all) degradants selected from TBZ01, TBZ02, and TBZ4; and/or (2) no drug crystals are observed (e.g., visually observed). In some embodiments, all of the degradants TBZ01, TBZ02, and TBZ04 are not detected by HPLC or below the limit for quantification in a shelf stable device or composition herein after shelf storage at 40 □ for 4 weeks. Exemplary conditions for HPLC analysis and retention times of TBZ01, TBZ02, and TBZ04 are shown in Example 5. However, when no antioxidant is used or the added antioxidant is BHT, degradants (including TBZ01, TBZ02, and TBZ04) were formed. In some embodiments, the adhesive composition can comprise a gallate antioxidant. In some preferred embodiments, the adhesive composition can comprise propyl gallate. In some preferred embodiments, propyl gallate is the only antioxidant in the adhesive composition. In some embodiments, other antioxidants can be used in combination with the propyl gallate. In some embodiments, the adhesive composition can also include propyl gallate, citric acid, ascorbic acid, vitamin E or tocopherol acetate, or a combination thereof, as an antioxidant. When present, the antioxidant, such as propyl gallate, is typically present in an amount of about 0.001% to about 0.5% (e.g., about 0.01%, about 0.02%, about 0.03%, about 0.04%, about 0.05%) by weight of the adhesive composition.

The active ingredient is typically present in the adhesive composition in an amount of about 2% to about 30% by weight. Preferably, in some embodiments, the active ingredient can be present in the adhesive composition in an amount of about 2% to about 15% by weight, such as about 2% to about 10%, or about 2% to about 7% by weight. The tetrabenazine in the adhesive compositions herein is not limited to a particular enantiomer and can be in a racemic form, a substantially pure R,R-tetrabenazine (e.g., with less than 10%, less than 5%, less than 1%, or less than 0.1% of the S,S-isomer), a substantially pure S,S-tetrabenazine (e.g., with less than 10%, less than 5%, less than 1%, or less 0.1% of the R,R-isomer), or a mixture of R,R-tetrabenazine and S,S-tetrabenazine in any ratio. Similarly, the deuterated tetrabenazine in the adhesive compositions described herein is not limited to a particular enantiomer and can be in a racemic form, a substantially pure R,R-isomer, e.g., R,R-deutetrabenazine, (e.g., with less than 10%, less than 5%, less than 1%, or less than 0.1% of the S,S-isomer), a substantially pure S,S-isomer, e.g., S,S-deutetrabenazine, (e.g., with less than 10%, less than 5%, less than 1%, or less than 0.1% of the R,R-isomer), or a mixture of R,R-isomer and S,S-isomer in any ratio. In some embodiments, the only active ingredient in the adhesive composition is tetrabenazine, such as a substantially pure R,R-isomer of tetrabenazine. In some embodiments, the only active ingredient in the adhesive composition is deutetrabenazine, such as a substantially pure R,R-isomer of deutetrabenazine. In some embodiments, the adhesive compositions can also include other active ingredients, e.g., as described herein.

Typically, a crystallization inhibitor is also included in the adhesive composition to prevent formation of drug crystals upon storage. Such drug crystals could retard skin permeation of such adhesive compositions. Accordingly, in some embodiments, the adhesive composition can include a crystallization inhibitor in an amount effective to prevent formation of drug crystals after shelf storage for two weeks at ambient temperature. In some embodiments, the adhesive composition can include a crystallization inhibitor selected from a polyvinylpyrrolidone polymer (e.g., Kollidon K30 or K90F (manufactured by BASF), Plasdone K20/32 or Plasdone K90 (manufactured by Ashland Chemical)), a cross-linked polyvinylpyrrolidone polymer (e.g., Kollidon CL), a polyvinylpyrrolidone copolymer (e.g., Plasdone S-630Copovidone (Asland)), a cellulose based polymer (e.g., hydroxylpropyl methyl cellulose, ethyl cellulose, hydroxypropyl cellulose), a polycarboxylic acid polymer (e.g., Cabopol (manufactured by Lubrizol)), a polymethacrylate (e.g., Plastoid B, Eudragit E100, Eudragit L100-55 (manufactured by Evonik)), a polyethylene glycol, polyvinyl acetate and polyvinylcaprolactame-based graft copolymer (PVAc-PVCap-PEG) (e.g., Soluplus (BASF), and combinations thereof. In some embodiments, the crystallization inhibitor is not Kollidon VA64 (BASF).

In some preferred embodiments, the adhesive composition can include a crystallization inhibitor selected from a polymethacrylate (e.g., Plastoid B (copolymer of butyl methacrylate and methyl methacrylate), Eudragit E100, Eudragit L100-55 (manufactured by Evonik)), a polyethylene glycol, polyvinyl acetate and polyvinylcaprolactame-based graft copolymer (PVAc-PVCap-PEG) (e.g., Soluplus (BASF), and combinations thereof. For example, in some specific embodiments, the adhesive composition includes a copolymer of butyl methacrylate and methyl methacrylate, such as a polymer under tradename the Plastoid B, manufactured by Evonic. In some specific embodiments, the adhesive composition includes a polyethylene glycol, polyvinyl acetate and polyvinylcaprolactame-based graft copolymer, such as a polymer under the tradename Soluplus, manufactured by BASF. The crystallization inhibitor, when present in the adhesive composition, typically is in an amount of about 5% to about 40% by weight, such as about 10%, about 20%, about 30%, about 40%, by weight, or any range between the recited value.

In some specific embodiments, the present invention provides adhesive compositions with the following ingredients:

| | Percentage by weight (dry) | | |
|---|---|---|---|
| Ingredient | Typical | Preferred | More preferred |
| Active ingredient (e.g., tetrabenazine base) | 2-10% | 5-10% | 5-7% (eg., 6.8%, 7.1%) |
| Adhesive (PSA) (e.g., Duro-Tak 87-900A) | 50-97% | 60-95% | 65-95% (e.g., 72.9%, 92.5%) |
| Antioxidants (e.g., propyl gallate) | 0-1% | 0.001-0.5% | 0.01-0.1% (e.g., 0.05%) |
| Crystallization Inhibitors (e.g., Plastoid B, Soluplus) | 0-40% | 10-40% | 15-30% (e.g., 20%, 19.3%) |

The numeric values in the table should be understood as preceded by the term "about." Other ingredients can be optionally included. In some embodiments, the adhesive composition is free of a permeation enhancer. In some embodiments, the adhesive composition is free of isopropyl myristate. Suitable active ingredients, adhesives (e.g., non-reactive acrylate adhesive), antioxidants, and crystallization inhibitors include those described herein. For example, in some preferred embodiments, the active ingredient is tetrabenazine base (e.g., a substantially pure R,R-isomer), the adhesive is an acrylate polymer, such as non-reactive acrylate adhesive, preferably, a copolymer of hexylethyl acrylate and methyl acrylate, such as Duro-Tak 87-900A, antioxidant is preferably propyl gallate, and crystallization inhibitor is preferably a copolymer of butyl methacrylate and methyl methacrylate or a polyethylene glycol, polyvinyl acetate and polyvinylcaprolactame-based graft copolymer. In some embodiments, the present disclosure also provides a method of preparing an adhesive composition (e.g., described herein). In some embodiments, the method comprising mixing an active ingredient (e.g., tetrabenazine base), an adhesive, optionally an antioxidant, optionally a crystallization inhibitor, in a suitable solvent (e.g., ethanol, etc.) to form a wet adhesive composition. Suitable amounts and suitable active ingredients, adhesives, antioxidants, crystallization inhibitors include any of those described and preferred herein, e.g., discussed in this paragraph and the preceding 10 paragraphs. Other optional ingredients and amounts thereof are also described herein. In some embodiments, the method further comprising casting the wet adhesive composition onto a backing layer. In some embodiments, the method further comprising drying the wet adhesive composition. The products produced by the methods herein are also novel compositions.

The adhesive composition (e.g., the adhesive composition with a non-reactive acrylate adhesive described herein) is typically included in a transdermal delivery device, for example, as a drug layer or drug-in-adhesive layer. For example, in some embodiments, the present disclosure provides a transdermal delivery device, which includes a backing layer, any of the adhesive composition described herein (e.g., the adhesive composition with a non-reactive acrylate adhesive described herein as a drug layer or drug-in-adhesive layer), and a release liner. The transdermal delivery device can be cut into different sizes as desired, which is typically about 10 cm$^2$ to about 100 cm$^2$. Other patch designs are described herein. Preferably, the transdermal delivery device (and/or the adhesive composition, e.g., with a non-reactive acrylate adhesive described herein) herein is storage stable (or alternatively referred to as shelf stable), for example, with no drug crystals observed after shelf storage at 40° C. for 4 weeks, and/or with no drug degradation observed by HPLC after shelf storage at 40° C. for 4 weeks.

For example, in some embodiments, the transdermal delivery device (and/or the adhesive composition e.g., with a non-reactive acrylate adhesive described herein) herein can be storage stable for 4 weeks or more, 8 weeks or more, 12 weeks or more, 16 weeks or more, 6 months or more, 12 months or more, etc.

Typically, the transdermal delivery device (and/or the adhesive composition) herein can also be configured to achieve a desired skin permeability of the active ingredient (e.g., tetrabenazine or deutetrabenazine). For example, in some embodiments, the transdermal delivery device (e.g., comprising the adhesive composition with a non-reactive acrylate adhesive described herein) can deliver to a subject in need thereof about 0.01 mg/day/cm$^2$ to about 5 mg/day/cm$^2$ (e.g., about 0.01 mg/day/cm$^2$, about 0.02 mg/day/cm$^2$, about 0.05 mg/day/cm$^2$, about 0.1 mg/day/cm$^2$, about 0.2 mg/day/cm$^2$, about 0.5 mg/day/cm$^2$, about 1 mg/day/cm$^2$, about 2 mg/day/cm$^2$, about 5 mg/day/cm$^2$, or any ranges between the specified values) of the active ingredient (e.g., tetrabenazine or deutetrabenazine), for example, over a period of time selected from about 8 hours, about 12 hours, about 18 hours, about 24 hours, about 2 days, about 3 days, about 4 days, about 5 days, about 6 days, and about 7 days. In some embodiments, the transdermal delivery device (e.g., comprising the adhesive composition with a non-reactive acrylate adhesive described herein) can deliver more than about 5 mg/day/cm$^2$, for example, about 8 mg/day/cm$^2$, about 10 mg/day/cm$^2$, about 15 mg/day/cm$^2$, about 20 mg/day/cm$^2$, or any ranges between the recited values, of the drug (e.g., tetrabenazine or deutetrabenazine). In some embodiments, the transdermal delivery device (e.g., comprising the adhesive composition with a non-reactive acrylate adhesive described herein) can deliver less than about 0.1 mg/day/cm$^2$, such as about 0.01 mg/day/cm$^2$, about 0.02 mg/day/cm$^2$, about 0.05 mg/day/cm$^2$, about 0.1 mg/day/cm$^2$, or any ranges between the recited values, of the active ingredient (e.g., tetrabenazine or deutetrabenazine).

For example, in some embodiments, the adhesive composition of the transdermal delivery device comprises about 2% to about 10% by weight (e.g., about 2% to about 7%) of tetrabenazine, the transdermal delivery device (e.g., comprising the adhesive composition with a non-reactive acrylate adhesive described herein) provides one or more of the following skin flux characteristics when tested in vitro using human cadaver skin: a) a cumulative tetrabenazine permeated of about 0.5 µg/cm$^2$ to about 50 µg/cm$^2$ (e.g., about 1 µg/cm$^2$, about 5 µg/cm$^2$, about 10 µg/cm$^2$, about 15 µg/cm$^2$, about 20 µg/cm$^2$, about 50 µg/cm$^2$, or any ranges between the recited values) at 8 hours post administration based on the active surface area; b) a cumulative tetrabenazine permeated of about 5 g/cm$^2$ to about 500 µg/cm$^2$ (e.g., about 5 µg/cm$^2$, about 10 µg/cm$^2$, about 15 µg/cm$^2$, about 20 µg/cm$^2$, about 50 µg/cm$^2$, about 100 µg/cm$^2$, about 200 µg/cm$^2$, about 500 µg/cm$^2$, or any ranges between the recited values) at 24 hours post administration based on the active surface area; and c) a cumulative tetrabenazine permeated of about 10 µg/cm$^2$ to about 1000 µg/cm$^2$ (e.g., about 10 µg/cm$^2$, about 20 µg/cm$^2$, about 50 µg/cm$^2$, about 100 µg/cm$^2$, about 200 µg/cm$^2$, about 300 µg/cm$^2$, about 400 µg/cm$^2$, about 600 µg/cm$^2$, about 1000 µg/cm$^2$, or any ranges between the recited values) at 48 hours post administration based on the active surface area. In some embodiments, the in vitro test is conducted in accordance with the method described in Example 6 of this application.

Methods of Administering Tetrabenazine

In various embodiments, the present invention further provides a method of using the transdermal delivery device or pharmaceutical compositions (e.g., adhesive compositions herein) described herein. In some embodiments, the transdermal delivery devices or pharmaceutical compositions can be used for any indication for which inhibition of VMAT-2 is beneficial. In some embodiments, the transdermal delivery devices or pharmaceutical compositions can be used for treating or preventing a disease or disorder mediated by VMAT-2. In some embodiments, the transdermal delivery devices or pharmaceutical compositions can be used for any indication for which administering tetrabenazine or deuterated tetrabanazine is beneficial. For example, in addition to the indication of chorea associated with Huntington's disease, other indications approved for use or associated with tetrabenazine or deuterated tetrabenazine include hemiballismus, tic disorders, tardive dyskinesia, and Tourette's syndrome. And in various embodiments, the transdermal delivery devices or pharmaceutical compositions can also be used for any of these indications.

In some embodiments, the present invention provides a method of administering tetrabenazine, deuterated tetrabenazine, or a combination thereof to a subject (e.g., human subject) in need thereof. In some embodiments, the method comprises applying any of the transdermal delivery devices or pharmaceutical compositions (e.g., adhesive compositions herein) to the subject, for example, to the skin of the subject. In some embodiments, the subject (e.g., human subject) is characterized as having a hyperkinetic movement disorder (e.g., a chronic hyperkinetic movement disorder). In some embodiments, the hyperkinetic movement disorder is selected from chorea associated with Huntington's disease, Wilson's disease, Tourette syndrome, restless leg syndrome, tardive dyskinesia, tic, and combinations thereof. In some embodiments, the method comprises applying a transdermal delivery device comprising tetrabenazine (e.g., a substantially pure R,R-tetrabenazine). In some embodiments, the method comprises applying a transdermal delivery device comprising deutetrabenazine (e.g., a substantially pure R,R-deutetrabenazine).

In some embodiments, the present invention also provides a method of inhibiting VMAT-2 in a subject in need thereof. In some embodiments, the method comprises applying any of the transdermal delivery devices or pharmaceutical compositions (e.g., adhesive compositions herein) to the subject, for example, to the skin of the subject.

In some embodiments, the present invention also provides a method of treating a vesicular monoamine transporter isoform 2 (VMAT2) mediated disease or disorder in a subject (e.g., a human subject) in need thereof. In some embodiments, the method comprises applying any of the transdermal delivery devices or pharmaceutical compositions (e.g., adhesive compositions herein) to the subject, for example, to the skin of the subject. VMAT2-mediated diseases or disorders, include, but are not limited to, hyperkinetic movement disorders (e.g., chronic hyperkinetic movement disorders). Huntington's disease, hemiballismus, senile chorea, tic disorders, tardive dyskinesia, dystonia, Tourette's syndrome, depression, cancer, rheumatoid arthritis, psychosis, multiple sclerosis, asthma, and/or any disorder which can lessened, alleviated, or prevented by administering a VMAT2 inhibitor. In some embodiments, the VMAT2-mediated disease or disorder is tardive dyskinesia. In some embodiments, the VMAT2-mediated disease or disorder is Huntington's disease. In some embodiments, the VMAT2-mediated disease or disorder is hemiballismus. In some embodiments, the VMAT2-mediated disease or disorder is Tourette's syndrome.

In some specific embodiments, the present invention provides a method of treating a hyperkinetic movement disorder in a subject (e.g., human subject) in need thereof. In some embodiments, the method comprises applying any of the transdermal delivery devices or pharmaceutical compositions (e.g., adhesive compositions herein) to the subject, for example, to the skin of the subject. In some embodiments, the hyperkinetic movement disorder is a chronic hyperkinetic movement disorder. In some embodiments, the hyperkinetic movement disorder is chorea associated with Huntington's disease, Wilson's disease, Tourette syndrome, restless leg syndrome, tardive dyskinesia, and/or a tic. In some embodiments, the hyperkinetic movement disorder is chorea associated with Huntington's disease. In some specific embodiments, the present invention provides a method of treating chorea associated with Huntington's disease in a subject in need thereof, the method comprising applying any of the transdermal delivery devices or pharmaceutical compositions (e.g., adhesive compositions herein) to the subject, for example, to the skin of the subject. In some specific embodiments, the present invention provides a method of treating tardive dyskinesia in a subject in need thereof, the method comprising applying any of the transdermal delivery devices or pharmaceutical compositions (e.g., adhesive compositions herein) to the subject, for example, to the skin of the subject. In some specific embodiments, the present invention provides a method of treating Tourette syndrome in a subject in need thereof, the method comprising applying any of the transdermal delivery devices or pharmaceutical compositions (e.g., adhesive compositions herein) to the subject, for example, to the skin of the subject. In some specific embodiments, the present invention provides a method of treating a tic in a subject in need thereof, the method comprising applying any of the transdermal delivery devices or pharmaceutical compositions (e.g., adhesive compositions herein) to the subject, for example, to the skin of the subject. In some specific embodiments, the present invention provides a method of treating hemiballismus in a subject in need thereof, the method comprising applying any of the transdermal delivery devices or pharmaceutical compositions (e.g., adhesive compositions herein) to the subject, for example, to the skin of the subject.

Tetrabenazine and/or a deuterated tetrabenazine (e.g., deutetrabenazine) can be used for the methods herein. Typically, the method comprises applying a transdermal delivery device herein which includes either tetrabenazine or deutetrabenazine as the only active ingredient. In some embodiments, the method comprises applying a transdermal delivery device herein which comprises a substantially pure R,R-tetrabenazine, e.g., with the substantially pure R,R-tetrabenazine as the only active ingredient. In some embodiments, the method comprises applying a transdermal delivery device herein which comprises a substantially pure R,R-deutetrabenazine e.g., with the substantially pure R,R-deutetrabenazine as the only active ingredient.

In any of the embodiments described herein, the method can comprise administering to the subject about 0.1 mg/day/cm$^2$ to about 5 mg/day/cm$^2$ (e.g., about 0.1 mg/day/cm$^2$, about 0.2 mg/day/cm$^2$, about 0.5 mg/day/cm$^2$, about 1 mg/day/cm$^2$, about 2 mg/day/cm$^2$, about 5 mg/day/cm$^2$, or any ranges between the specified values) of the drug (e.g., tetrabenazine or deutetrabenazine), for example, over a period of time selected from about 8 hours, about 12 hours, about 18 hours, about 24 hours, about 2 days, about 3 days, about 4 days, about 5 days, about 6 days, and about 7 days. However, in some embodiments, the method can comprise administering to the subject more than about 5 mg/day/cm$^2$, for example, about 8 mg/day/cm$^2$, about 10 mg/day/cm$^2$, about 15 mg/day/cm$^2$, about 20 mg/day/cm$^2$, or any ranges between the recited values, of the drug (e.g., tetrabenazine or deutetrabenazine). In some embodiments, the method can also comprise administering to the subject less than about 0.1 mg/day/cm$^2$, such as about 0.01 mg/day/cm$^2$, about 0.02 mg/day/cm$^2$, about 0.05 mg/day/cm$^2$, about 0.1 mg/day/cm$^2$, or any ranges between the recited values, of the drug (e.g., tetrabenazine or deutetrabenazine).

In some embodiments, the present invention provides a method of treating a vesicular monoamine transporter isoform 2 (VMAT2) mediated disease or disorder in a subject (e.g., a human subject) in need thereof, comprising transdermally administering to the subject a therapeutically effective amount of tetrabenazine or deutetrabenazine. Suitable VMAT2 mediated diseases or disorders are described herein.

Various advantages are associated with the methods described herein. For example, in some embodiments, the method can decrease inter-individual variation in plasma levels of tetrabenazine or deutetrabenazine or a metabolite thereof compared to equal doses of oral administration of tetrabenazine or deutetrabenazine. In some embodiments, the method can decrease Cmax (e.g., by 10%, 40%, 60%, or more) of tetrabenazine or deutetrabenazine or a metabolite thereof compared to equal doses of oral administration of tetrabenazine or deutetrabenazine, for example, without also reducing therapeutic efficacy. In some embodiments, the method can provide similar plasma levels of tetrabenazine or deutetrabenazine or a metabolite thereof when equal doses are administered to subjects who are genotyped based on CYP2D6 expression as poor metabolizer (PM), intermediate metabolizer (IM), or extensive metabolizer (EM). In some embodiments, the same dose or substantially the same dose of tetrabenazine or deutetrabenazine can be administered to subjects who are characterized as PM, IM, or EM. In some embodiments, the methods herein can transdermally administer the drug (e.g., tetrabenazine or deutetrabenazine) to the subject without regard to whether the subject is characterized as PM, IM, or EM based on CYP2D6 expression.

Combination Therapy

The transdermal delivery devices or pharmaceutical compositions disclosed herein (e.g., adhesive compositions herein) may also be combined or used in combination with other agents useful in the treatment of VMAT2-mediated disorders. Such other agents can be administered, by a route and in an amount commonly used therefor, simultaneously or sequentially with the transdermal delivery devices or pharmaceutical compositions disclosed herein (e.g., adhesive compositions herein). In some embodiments, such other agents are included in the transdermal delivery devices or pharmaceutical compositions disclosed herein (e.g., adhesive compositions herein). However, in some embodiments, such other agents are administered as a separate composition or otherwise independent of the transdermal delivery devices or pharmaceutical compositions disclosed herein (e.g., adhesive compositions herein).

In some embodiments, the transdermal delivery devices or pharmaceutical compositions disclosed herein (e.g., adhesive compositions herein) can be used in combination with one or more anti-psychotics, including, but not limited to, chlorpromazine, levomepromazine, promazine, acepromazine, triflupromazine, cyamemazine, chlorproethazine, dixyrazine, fluphenazine, perphenazine, prochlorperazine, thiopropazate, trifluoperazine, acetophenazine, thioproperazine, butaperazine, perazine, periciazine, thioridazine, mesoridazine, pipotiazine, haloperidol, trifluperidol, melperone, moperone, pipamperone, bromperidol, benperidol, droperidol, fluanisone, oxypertine, molindone, sertindole, ziprasidone, flupentixol, clopenthixol, chlorprothixene, thiothixene, zuclopenthixol, fluspirilene, pimozide, penfluridol, loxapine, clozapine, olanzapine, quetiapine, tetrabenazine, sulpiride, sultopride, tiapride, remoxipride, amisulpride, veralipride, levosulpiride, lithium, prothipendyl, risperidone, clotiapine, mosapramine, zotepine, pripiprazole, and paliperidone.

In some embodiments, the transdermal delivery devices or pharmaceutical compositions disclosed herein (e.g., adhesive compositions herein) can be used in combination with one or more benzodiazepines ("minor tranquilizers"), including, but not limited to alprazolam, adinazolam, bromazepam, camazepam, clobazam, clonazepam, clotiazepam, cloxazolam, diazepam, ethyl loflazepate, estizolam, fludiazepam, flunitrazepam, halazepam, ketazolam, lorazepam, medazepam, dazolam, nitrazepam, nordazepam, oxazepam, potassium clorazepate, pinazepam, prazepam, tofisopam, triazolam, temazepam, and chlordiazepoxide.

In some embodiments, the transdermal delivery devices or pharmaceutical compositions disclosed herein (e.g., adhesive compositions herein) can be used in combination with olanzapine or pimozide.

In some embodiments, the transdermal delivery devices or pharmaceutical compositions disclosed herein (e.g., adhesive compositions herein) can be used in combination with other classes of compounds, including, but not limited to, anti-retroviral agents; CYP3A inhibitors; CYP3A inducers; protease inhibitors; adrenergic agonists; anti-cholinergics; mast cell stabilizers; xanthines; leukotriene antagonists; glucocorticoids treatments; local or general anesthetics;

non-steroidal anti-inflammatory agents (NSAIDs), such as naproxen; antibacterial agents, such as amoxicillin; cholesteryl ester transfer protein (CETP) inhibitors, such as anacetrapib; anti-fungal agents, such as isoconazole; sepsis treatments, such as drotrecogin-α; steroidals, such as hydrocortisone; local or general anesthetics, such as ketamine; norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothlazide, hydrochiorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as pacitaxel, docetaxel, and epothilones A-F; plant-derived products, such as *vinca* alkaloids, epipodophyllotoxins, and taxanes; and topoisomerase inhibitors; prenyl-protein transferase inhibitors; and cyclosporine; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

In some embodiments, the transdermal delivery devices or pharmaceutical compositions disclosed herein (e.g., adhesive compositions herein) can be used in combination with dextromethorphan, and/or a cannabinoid, such as cannabidiol.

Definitions

As used herein, the term "about" modifying an amount related to the invention refers to variation in the numerical quantity that can occur, for example, through routine testing and handling; through inadvertent error in such testing and handling; through differences in the manufacture, source, or purity of ingredients/materials employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, "coat weight" of a drug layer refers to the weight of the drug layer (e.g., a drug-in-adhesive layer or a drug-in-reservoir layer) per unit area of the active surface area of the transdermal drug delivery system.

As used herein, the term "cumulative drug permeated" refers to the total amount of drug permeated per square centimeter during a given period of time. Unless otherwise obvious from context, "cumulative drug permeated" at a given time (e.g., at 24 hours post administration) refers to the total amount of drug permeated per square centimeter from time 0 (i.e., time of administration) to the given time. Unless otherwise obvious from context, "cumulative drug permeated" refers to the arithmetic mean value measured and/or calculated in accordance with the methods described herein. The term "mean value" as used herein, when not specified, also refers to arithmetic mean value, unless contradictory to common practice in the field.

As used herein, the term "flux" refers to the quantity of the drug permeated skin per unit area per unit time. Unless otherwise obvious from context, "flux" refers to the arithmetic mean value measured and/or calculated in accordance with the methods described herein. A typical unit of flux is milligram per square centimeter per hour.

Flux rate as referenced in this patent application can mean that measured by either in vivo or in vitro methods. One way to measure flux is to place the transdermal delivery device or formulation on a known skin area of a human volunteer and measure how much drug can permeate across skin within certain time constraints. In some embodiments, when specifically referenced as measured by in vitro method using human cadaver skin, the flux rate is measured in accordance with the method described in Example 3 or 6. Although an in vitro method uses human epidermal membrane obtained from a cadaver, rather than measure drug flux across the skin using human volunteers, it is generally accepted by those skilled in the art that results from a properly designed and executed in vitro test can be used to estimate or predict the results of an in vivo test with reasonable reliability.

The terms "skin flux characteristics" and "flux characteristics" are used interchangeably herein.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated.

The term "therapeutically effective amount," as used herein, refers to that amount of a therapeutic agent (e.g., tetrabenazine) sufficient to result in amelioration of one or more symptoms of a disorder or condition (e.g., Huntington's disease), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment.

As used herein, applying or administering the transdermal delivery device herein should be understood as in accordance with how such transdermal delivery device is normally applied or administered, e.g., to the skin of a human subject.

The term "chronic hyperkinetic movement disorders" refers to disorders characterized by non-purposeful, repetitive, disordered motor acts, variously termed "compulsive", "rhythmical", or "stereotyped." In humans, chronic hyperkinetic movement disorders can be psychogenic (e.g., tics), idiopathic (as in, e.g., Tourette's syndrome and Parkinson's Disease, genetic (as in, e.g., the chorea characteristic of Huntington's Disease), infectious (as in, e.g., Sydenham's Chorea), or, as in tardive dyskinesia, drug-induced. Unless otherwise stated, "chronic hyperkinetic movement disorders" refers to and includes all psychogenic, idiopathic, genetic, and drug-induced movement disorders.

The term "stereotyped" refers to a repeated behavior that appears repetitively with slight variation or, less commonly, as a complex series of movements.

The term "VMAT2" refers to vesicular monoamine transporter 2, an integral membrane protein that acts to transport monoamines—particularly neurotransmitters such as dopamine, norepinephrine, serotonin, and histamine—from cellular cytosol into synaptic vesicles.

The term "VMAT2-mediated disorder," refers to a disorder that is characterized by abnormal VMAT2 activity. A VMAT2-mediated disorder may be completely or partially mediated by modulating VMAT2. In particular, a VMAT2-mediated disorder is one in which inhibition of VMAT2 results in some effect on the underlying disorder e.g., administration of a VMAT2 inhibitor results in some improvement in at least some of the patients being treated.

Exemplary Embodiments 1-32

The following shows certain exemplary embodiments (Embodiments 1-32) of the present disclosure.

Embodiment 1. A transdermal delivery device comprising:
   a backing layer,
   a drug layer comprising tetrabenazine in an amount of about 2% to about 30% by weight of the drug layer, and
   an adhesive layer defining an active surface area,
   wherein the transdermal delivery device provides one or more of the following skin flux characteristics when tested in vitro using human cadaver skin:
   (a) a cumulative tetrabenazine permeated of about 0.1 $\mu g/cm^2$ to about 150 $\mu g/cm^2$ at 6 hours post administration based on the active surface area;
   (b) a cumulative tetrabenazine permeated of about 2 $g/cm^2$ to about 400 $\mu g/cm^2$ at 12 hours post administration based on the active surface area; and
   (c) a cumulative tetrabenazine permeated of about 5 $g/cm^2$ to about 1000 $\mu g/cm^2$ at 24 hours post administration based on the active surface area.

Embodiment 2. The transdermal delivery device of embodiment 1, wherein the tetrabenazine is present in an amount of about 2% to about 5% by weight of the drug layer, wherein the transdermal delivery device provides one or more of the following skin flux characteristics when tested in vitro using human cadaver skin:
   (i) a cumulative tetrabenazine permeated of about 0.1 $\mu g/cm^2$ to about 100 $\mu g/cm^2$ at 6 hours post administration based on the active surface area;
   (ii) a cumulative tetrabenazine permeated of about 2 $\mu g/cm^2$ to about 200 $\mu g/cm^2$ at 12 hours post administration based on the active surface area;
   (iii) a cumulative tetrabenazine permeated of about 5 $g/cm^2$ to about 600 $\mu g/cm^2$ at 24 hours post administration based on the active surface area.

Embodiment 3. The transdermal delivery device of embodiment 1, wherein the tetrabenazine is present in an amount of about 10% to about 15% by weight of the drug layer, wherein the transdermal delivery device provides one or more of the following skin flux characteristics when tested in vitro using human cadaver skin:
   (i) a cumulative tetrabenazine permeated of about 0.5 $\mu g/cm^2$ to about 150 $\mu g/cm^2$ at 6 hours post administration based on the active surface area;
   (ii) a cumulative tetrabenazine permeated of about 4 $\mu g/cm^2$ to about 400 $\mu g/cm^2$ at 12 hours post administration based on the active surface area; and
   (iii) a cumulative tetrabenazine permeated of about 6 $g/cm^2$ to about 1000 $\mu g/cm^2$ at 24 hours post administration based on the active surface area.

Embodiment 4. The transdermal delivery device of embodiment 1, wherein the tetrabenazine is present in an amount of about 8% by weight of the drug layer.

Embodiment 5. The transdermal delivery device of any one of embodiments 1-4, wherein the active surface area is about 5 $cm^2$ to about 300 $cm^2$.

Embodiment 6. The transdermal delivery device of any one of embodiments 1-5, wherein the active surface area is about 10 $cm^2$ to about 100 $cm^2$.

Embodiment 7. The transdermal delivery device of any one of embodiments 1-6, which is a drug-in-reservoir patch, wherein the drug layer is a reservoir comprising tetrabenazine.

Embodiment 8. The transdermal delivery device of any one of embodiments 1-6, which is a drug-in-adhesive patch, wherein the drug layer comprises tetrabenazine dispersed in a pressure sensitive adhesive.

Embodiment 9. The transdermal delivery device of embodiment 8, comprising a single drug layer.

Embodiment 10. The transdermal delivery device of embodiment 8 or 9, wherein the pressure sensitive adhesive comprises a polyisobutylene (PIB) adhesive, a silicone polymer adhesive (e.g., Bio-7-4202), an acrylate copolymer adhesive (e.g., Duro-Tak 87-2287), or a combination thereof.

Embodiment 11. The transdermal delivery device of any one of embodiments 1-10, wherein the drug layer further comprises a permeation enhancer, an additional active ingredient, a humectant, a plasticizer, a gel-forming agent, an antioxidant, an anti-irritant, a drug release modifier, a solvent, a crystallization inhibitor, or a combination thereof.

Embodiment 12. The transdermal delivery device of any one of embodiments 1-11, wherein the drug layer has a coat weight of about 0.1 $g/cm^2$ to about 0.5 $g/cm^2$ active surface area.

Embodiment 13. The transdermal delivery device of any one of embodiments 1-12, which is capable of adhering continuously to the skin of a user for about 8 hours, about 12 hours, about 18 hours, about 24 hours, about 2 days, about 3 days, about 4 days, about 5 days, about 6 days, or about 7 days or more.

Embodiment 14. The transdermal delivery device of any one of embodiments 1-13, wherein the tetrabenazine is a substantially pure R,R-isomer.

Embodiment 15. A method of administering tetrabenazine to a human subject in need thereof, comprising applying the transdermal delivery device of any one of embodiments 1-14 to the skin of the human subject.

Embodiment 16. The method of embodiment 15, wherein the human subject is characterized as having a hyperkinetic movement disorder (e.g., a chronic hyperkinetic movement disorder).

Embodiment 17. The method of embodiment 16, wherein the hyperkinetic movement disorder is chorea associated with a disease or disorder selected from Huntington's disease, Wilson's disease, Tourette syndrome, restless leg syndrome, tardive dyskinesia, tic, and combinations thereof.

Embodiment 18. A method of inhibiting a vesicular monoamine transporter isoform 2 (VMAT2) in a subject, the method comprising applying the transdermal delivery device of any one of embodiments 1-14 to the skin of the subject.

Embodiment 19. A method of treating a vesicular monoamine transporter isoform 2 (VMAT2) mediated disease or disorder in a subject in need thereof, the method comprising applying the transdermal delivery device of any one of embodiments 1-14 to the skin of the subject.

Embodiment 20. A method of treating a hyperkinetic movement disorder in a subject in need thereof, comprising applying the transdermal delivery device of any one of embodiments 1-14 to the skin of the subject.

Embodiment 21. The method of embodiment 20, wherein the hyperkinetic movement disorder is a chronic hyperkinetic movement disorder.

Embodiment 22. The method of embodiment 20 or 21, wherein the hyperkinetic movement disorder is chorea associated with Huntington's disease, Wilson's disease, Tourette syndrome, restless leg syndrome, tardive dyskinesia, and/or a tic.

Embodiment 23. An adhesive composition comprising tetrabenazine homogeneously dispersed in a pressure sensitive adhesive, wherein the adhesive composition is capable of adhering continuously to the skin of a user for an extended period of time selected from about 8 hours, about 12 hours, about 18 hours, about 24 hours, about 2 days, about 3 days, about 4 days, about 5 days, about 6 days, or about 7 days or more.

Embodiment 24. The adhesive composition of embodiment 23, wherein the pressure sensitive adhesive comprises a polyisobutylene (PIB) adhesive, a silicone polymer adhesive, an acrylate copolymer adhesive, or a combination thereof.

Embodiment 25. The adhesive composition of embodiment 23 or 24, further comprising a permeation enhancer.

Embodiment 26. The adhesive composition of any one of embodiments 23-25, wherein the tetrabenazine is a substantially pure R,R-isomer.

Embodiment 27. The adhesive composition of any one of embodiments 23-26, wherein the tetrabenazine is present in an amount of about 2% to about 30% by weight of the adhesive composition.

Embodiment 28. A transdermal delivery device comprising:
 a backing layer,
 the adhesive composition of any one of embodiments 23-27; and
 a release liner.

Embodiment 29. A method of treating a hyperkinetic movement disorder in a subject in need thereof, the method comprising applying the adhesive composition of any of embodiments 23-27 or the transdermal delivery device of embodiment 28 to the skin of the subject.

Embodiment 30. The method of embodiment 29, wherein the hyperkinetic movement disorder is a chronic hyperkinetic movement disorder.

Embodiment 31. The method of embodiment 29 or 30, wherein the hyperkinetic movement disorder is chorea associated with Huntington's disease, tardive dyskinesia, Tourette's syndrome, and/or a tic.

Embodiment 32. A method of treating a hyperkinetic movement disorder in a subject in need thereof, the method comprising transdermally administering a therapeutically effective amount of tetrabenazine or deuterated tetrabenazine to the subject.

EXAMPLES

Example 1. Preparation of Tetrabenazine Transdermal Patch

This example shows one procedure for preparing tetrabenazine drug-in-adhesive patch. Tetrabenazine base is generally commercially available in high purity (e.g., 99%), for example, from Octagon Chemical Ltd, Hangzhou, China, via internet on "Alibaba" website.

In this example, tetrabenazine base was thoroughly mixed into the adhesive, Durotak 87-2287 (manufactured by Henkel Adhesives) until the mixture was homogenous. Afterwards, the adhesive mixture was dispensed on a release liner using the "draw down knife" and forced dried for 1.5 min using a typical hair drier followed by lamination to a backing film.

The adhesive mixtures can contain tetrabenazine in different concentrations. In this example, four concentrations were used: 1) 2.5% formulation, prepared from mixing 2.5% tetrabenazine with 97.5% Durotak 87-2287; 2) 5% formulation, prepared from mixing 5% tetrabenazine with 95% Durotak 87-2287; 3) 10% formulation, prepared from mixing 10% tetrabenazine with 90% Durotak 87-2287; and 4) 15% formulation, prepared from mixing 15% tetrabenazine with 85% Durotak 87-2287. All percentages for tetrabenazine and Durotak refer to weight percentage based on final weight of the respective formulations.

Example 2. Tetrabenazine Transdermal Patch with Two Adhesives

Following the same procedure of Example 1, tetrabenazine transdermal patches with a mixture of two different adhesives at different ratios were also prepared, with the concentration of tetrabenazine being kept at 10% by weight.

The two adhesives used in this Example were a silicone polymer (BIO-7-4202 from Dow Corning Co.) and an acrylate copolymer (Durotak 87-2287). Four different ratios were used in this example: 1) 5/95 (Durotak 87-2287/BIO-7-4202); 2) 10/90 (Durotak 87-2287/BIO-7-4202); 3) 25/75 (Durotak 87-2287/BIO-7-4202); and 4) 50/50 (Durotak 87-2287/BIO-7-4202).

Example 3. Transdermal Flux Test

Transdermal flux of Tetrabenazine from the patch was tested using human cadaver epidermis by Franz Diffusion Cell method. The cadaver epidermis was obtained from Health Science Tissue Bank in Phoenix AZ.

The transdermal flux of Tetrabenazine through human cadaver epidermis was analyzed using the following HPLC method.

Mobile Phase: 55/45 Acetonitrile/Water—0.05% Triethylamine adjusted pH-6.5

HPLC Column: Kinetex C18, 150×4.6 mm, 5 m from Pheneomenex

Wavelength: 230 nm, Flow: 1.2 mL/min

The patches in Examples 1 and 2 were tested and the transdermal flux results are presented in FIGS. 1 and 2, respectively.

As shown in FIG. 1, the highest transdermal flux observed for patches in Example 1 is the adhesive matrix with 10% Tetrabenazine concentration.

As shown in FIG. 2, varying the ratio of the silicone polymer to acrylate copolymer does not significantly change the flux characteristics. However, when compared to the results shown in FIG. 1, the flux observed for patches prepared according to Example 2 is noticeably lower than the flux from the patch with 10% Tetrabenazine concentration prepared in Example 1.

Thus, adding a silicone adhesive to an acrylate adhesive (e.g., Durotak 87-2877) may be able to slow the flux rate of tetrabenazine.

Example 4A. Preparation of Tetrabenazine in Adhesives with No Functional Groups

| | | Batch composition | | | |
|---|---|---|---|---|---|
| Ingredient | Function | wet grams | solids % | dry grams | dry % |
| Tetrabenazine (+) (TBZ) | Active Ingredient | 4.25 | | 4.25 | 7.1% |
| Ethyl acetate | Solvent | 10.00 | | | |
| Ethanol | Solvent | 5.00 | | | |
| DuroTak 87-900A | Adhesive | 100.0 | 43.70% | 43.70 | 72.9% |
| Propyl Gallate | Antioxidant | 0.030 | | 0.030 | 0.050% |
| Plastoid B | Crystallization Inhibitor/solubilizer | 12.00 | | 12.000 | 20.0% |
| total | | 119.25 | | 59.98 | 100.0% |

Plastoid B is a copolymer of butyl methacrylate and methyl methacrylate, manufactured by Evonik.

Procedure for Preparation

The following procedure was followed for the preparation of the patch in Example 4A. In a 50-mL beaker, dissolve propyl gallate in ethanol by hand mixing. Separately, in a 250-mL beaker, add in Ethyl acetate, mix with a mechanical stirrer at low speed. Add in TBZ, and follow by Plastoid B powder while mixing. When Plastoid B dissolved, add in weighed DuroTak 87-900A while mixing. Mix, at moderate speed, for 30 min. or till homogeneous. Cast the solution, using a 10-mil coating applicator on 3M's backing film, Scotchpak 9723 film. Air dry the casting for 10 min, and oven dry at 85° C. for 10 min. Cover the dried adhesive with split Loparex release liners. Die cut the covered coating into 60 cm2 patches, using a steel rule die.

The patch has good skin adhesion and shear strength, and adheres snugly on skin for more than 48 hours.

The patch was die-cut to fix on the Franz cells for skin permeation study. The test results are reported in Example 6.

No crystals were observed on the patch for 4 weeks at 40° C., indicating good physical stability of the transdermal patch formulation. No degradation was observed on the patch for 4 weeks at 40° C., indicating good chemical stability of the transdermal patch formulation.

Examples 4B and 4C. Preparation of Tetrabenazine in Adhesives with No Functional Groups Two similar formulations were prepared following the same procedure as shown in Example 4A. These are given in the following table (dry composition):

| Formulation | Function | Ex 4B | Ex 4C |
|---|---|---|---|
| TBZ(+) | Active | 7.0% | 7.1% |
| DT 87-900A | Adhesive | 92.5% | 72.9% |
| Propyl gallate | Antioxidant | 0.05% | 0.05% |
| Soluplus | Crystal Inhibitor/solubilizer | | 20.0% |

The patches prepared in Examples 4B and 4C were also tested for skin permeation study.

Example 5. Stability Studies of Tetrabenazine Patch Formulations

Various patch formulations of tetrabenazine were prepared and tested for chemical and/or physical stabilities. The inventors found that patch Formulations prepared with DuroTak 87-2287 or Duro-Tak 87-2677 Adhesives, which contains Functional Groups, showed yellowish color after shelf storage at 40 ☐ for 4 weeks, indicating instability of the active ingredient due to oxidation and/or other degradation. DuroTak 87-2287 has hydroxyl functional groups of —OH and epoxy, and DuroTak 87-2677 has acidic functional group of —COOH. In contrast, patch formulations prepared using DuroTak 87-900A, which do not have any functional groups, were found to be stable for 4 weeks at 40° C., see Example 4A.

The inventors also found that patch Formulations prepared without propyl gallate as antioxidants result in degradation of active ingredients. Impurities (drug-related) such as TBZ 01, TBZ 02, and TBZ 04 were formed and detected by HPLC, if no antioxidant is used. Antioxidants that can prevent oxidation and/or other degradation of TBZ include propyl gallate, citric acid, ascorbic acid, vitamin E (tocopherol acetate), etc.

Tetrabenazine and related compounds were analyzed using isocratic reversed phase HPLC with UV detector.

Column: Gemini C18, 4.6×150 mm, 5 μm particle size, or equivalent.
Column temperature: 45° C.
Injection Volume: 10 μL
Detection Wavelength: 210 nm
Mobile Phase: Ratio of Mobile Phase A/Mobile Phase B=44:56
Mobile Phase A: 10 mM $K_2HPO_4$ in $H_2O$
Mobile Phase B: Acetonitrile
Flow Rate: 1.2 m/min
Run Time: 12 min
Retention Time: about 5.5 min for tetrabenazine
Retention times for Imurityl (TBZ01) is at about 1.95 min; Impurity 2 (TBZ02) is at about 3.10 min; and Impurity 4 (TBZ04) is at about 5.29 min.

The inventors further found that without use of Soluplus or Plastoid B as crystallization inhibitor/solubilizer, see e.g., Example 4B, crystals appeared on the patch after shelf storage for 2 weeks at ambient temperature. Formation of crystals retards the skin permeation of the patch formulations.

Thus, preferred composition should contain crystallization inhibitors so that the active ingredient remains in the adhesive matrix in amorphous form for at least 12 months of storage at room temperature. Crystallization inhibitors preferred include:

PVP (polyvinylpyrrolidone) polymers: Kollidon K30 or K90F (manufactured by BASF), Plasdone K20/32 or Plasdone K90 (manufactured by Ashland Chemical).

Crosslink PVP polymers: Kollidon CL

PVP copolymers (copovidones): Plasdone S-630Copovidone (Asland)

Cellulose-based polymers: Hydroxylpropyl methyl cellulose (HPMC/Methocel), ethyl cellulose (Ethocel by Dow Chemica) e.g, Hydroxylpropyl cellulose (HPC, e.g. Klucel by Ashland)

Polycarboxylic acid polymers: Carbopol (manufactured by Lubrizol)

Polymethacrylates: Plastoid B, Eudragit E100, Eudragit L100-55 (manufactured by Evonik)

Soluplus (BASF): a polyethylene glycol, polyvinyl acetate and polyvinylcaprolactame-based graft copolymer (PVAc-PVCap-PEG)

Example 6. Skin Permeation Studies

Patch formulations prepared in Examples 4A-4C were used for a skin permeation study using the following protocol:

Franz cell assembly—Logan Instruments (6-cell unit)
Each cell has 12 mL volume, 1.5 cm diameter orifice
Receptor medium was a phosphate buffer solution (PBS) pH 7.4
Cell temperature was maintained at 37° C.
Sampling method: took 1.5 mL for HPLC assay, emptied cell, replaced with fresh medium
Sampling time points: 2, 4, 8, 12, 24 and 48 hours
Cadaver skin was used and was obtained from New York Fighters Skin Bank.
Assay method for media: HPLC.

RESULTS of the study are presented in the table and the plot below. The values presented are cumulative amount of TBZ permeated per cm2 (i.e. μg/cm2). See also FIG. 3.

| AVERAGE | 2 h | 4 h | 8 h | 24 h | 48 h |
|---------|-----|-----|-----|------|------|
| Ex 4B | 0.00 | 1.95 | 4.07 | 25.61 | 64.56 |
| Ex 4C | 0.00 | 0.05 | 1.36 | 17.38 | 48.59 |
| Ex 4A | 0.00 | 0.47 | 5.38 | 32.27 | 73.99 |

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. An adhesive composition comprising:
    an active ingredient dispersed in a non-reactive acrylate pressure sensitive adhesive, wherein the active ingredient is selected from tetrabenazine, deuterated tetrabenazine, or a combination thereof; and
    a crystallization inhibitor which is a polyethylene glycol, polyvinyl acetate, and polyvinylcaprolactame based graft copolymer;
    wherein the non-reactive acrylate pressure sensitive adhesive is in an amount of about 50% to about 97% by weight, and wherein the non-reactive acrylate pressure sensitive adhesive does not have functional groups selected from epoxy, —OH, —COOH, and combinations thereof.

2. The adhesive composition of claim 1, wherein the non-reactive acrylate pressure sensitive adhesive is a copolymer of alkyl acrylate.

3. The adhesive composition of claim 1, wherein the non-reactive acrylate pressure sensitive adhesive is a copolymer of $C_2$-$C_{18}$ alkyl acrylate and methyl acrylate, and optionally one or more acrylamide monomers with no functional groups selected from epoxy, —OH, —COOH, and combinations thereof.

4. The adhesive composition of claim 1, wherein the non-reactive acrylate pressure sensitive adhesive is a copolymer of 2-ethyl hexyl acrylate, methyl acrylate, and tert octyl acrylamide.

5. The adhesive composition of claim 1, wherein the non-reactive acrylate pressure sensitive adhesive is free or substantially free of vinyl acetate.

6. The adhesive composition of claim 1, which is free of a permeation enhancer.

7. The adhesive composition of claim 1, which is free of isopropyl myristate.

8. The adhesive composition of claim 1, which is free of a permeation enhancer selected from fatty alcohols, fatty acids, fatty esters and combinations thereof.

9. The adhesive composition of claim 1, wherein the active ingredient is present in an amount of about 2% to about 7% by weight.

10. The adhesive composition of claim 1, further comprising a gallate antioxidant.

11. The adhesive composition of claim 1, further comprising propyl gallate in an amount of about 0.001% to about 0.5% by weight.

12. The adhesive composition of claim 1, wherein the crystallization inhibitor is in an amount effective to prevent formation of drug crystals after shelf storage for two weeks at ambient temperature.

13. The adhesive composition of claim 1, wherein the sole active ingredient is a substantially pure R,R-isomer of tetrabenazine.

14. The adhesive composition of claim 1, which is capable of adhering continuously to the skin of a user for about 8 hours, about 12 hours, about 18 hours, about 24 hours, about 2 days, about 3 days, about 4 days, about 5 days, about 6 days, or about 7 days.

15. A transdermal delivery device comprising:
    a backing layer,
    the adhesive composition of claim 1; and
    a release liner.

16. The transdermal delivery device of claim 15, which is shelf stable.

17. The transdermal delivery device of claim 15, which provides a subject user the active ingredient at a rate of about 0.01 mg/day/cm$^2$ to about 5 mg/day/cm$^2$ for a period of about 8 hours, about 12 hours, about 18 hours, about 24 hours, about 2 days, about 3 days, about 4 days, about 5 days, about 6 days, or about 7 days.

18. A method of administering tetrabenazine, deuterated tetrabenazine, or a combination thereof, to a subject in need thereof, comprising applying the adhesive composition of claim 1 to the skin of the subject.

19. The method of claim 18, wherein the subject is characterized as having a hyperkinetic movement disorder.

20. The method of claim 19, wherein the hyperkinetic movement disorder is selected from chorea associated with Huntington's disease, Wilson's disease, Tourette syndrome, restless leg syndrome, tardive dyskinesia, tic, and combinations thereof.

21. A method of inhibiting a vesicular monoamine transporter isoform 2 (VMAT2) in a subject in need thereof, the method comprising applying the adhesive composition of claim 1 to the skin of the subject.

22. A method of treating a vesicular monoamine transporter isoform 2 (VMAT2) mediated disease or disorder in a subject in need thereof, the method comprising applying the adhesive composition of claim 1 to the skin of the subject.

23. A method of treating a hyperkinetic movement disorder in a subject in need thereof, comprising applying the adhesive composition of claim 1 to the skin of the subject.

24. The method of claim 23, wherein the hyperkinetic movement disorder is a chronic hyperkinetic movement disorder.

25. The method of claim 23, wherein the hyperkinetic movement disorder is chorea associated with Huntington's disease, Wilson's disease, Tourette syndrome, restless leg syndrome, tardive dyskinesia, and/or a tic.

26. A transdermal delivery device comprising:
a backing layer;
an adhesive composition; and
a release liner;
wherein the adhesive composition comprises:
   a) an active ingredient dispersed in a non-reactive acrylate pressure sensitive adhesive, wherein the active ingredient is selected from tetrabenazine, deuterated tetrabenazine, or a combination thereof, and the non-reactive acrylate pressure sensitive adhesive is a copolymer of 2-ethyl hexyl acrylate, methyl acrylate, and tert octyl acrylamide,
   b) a crystallization inhibitor, which is a polyethylene glycol, polyvinyl acetate, and polyvinylcaprolactame-based graft copolymer, and
   c) propyl gallate,
      wherein the adhesive composition comprises by weight percentage:
         the active ingredient in an amount of about 2% to about 10% by weight,
         the non-reactive acrylate pressure sensitive adhesive in an amount of about 50% to about 90% by weight,
         the crystallization inhibitor in an amount of about 5% to about 40% by weight, and
         the propyl gallate in an amount of about 0.001% to about 0.5% by weight.

27. The transdermal delivery device of claim 26, which is characterized by having no drug crystals observed after shelf storage at 40° C. for 4 weeks and no drug degradation observed by high performance liquid chromatography after shelf storage at 40° C. for 4 weeks.

\* \* \* \* \*